(12) United States Patent
Sandahl et al.

(10) Patent No.: US 10,512,554 B2
(45) Date of Patent: Dec. 24, 2019

(54) PUMP SYSTEM

(71) Applicant: Ossur Iceland ehf, Reykjavik (IS)

(72) Inventors: David Sandahl, Reykjavik (IS); Dana Stewart Marlin, Reykjavik (IS); Hafsteinn Jonasson, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 170 days.

(21) Appl. No.: 15/685,488

(22) Filed: Aug. 24, 2017

(65) Prior Publication Data

US 2018/0055659 A1    Mar. 1, 2018

Related U.S. Application Data

(60) Provisional application No. 62/379,905, filed on Aug. 26, 2016.

(51) Int. Cl.
| | | |
|---|---|---|
| *A61F 2/80* | (2006.01) | |
| *A61F 2/66* | (2006.01) | |
| *A61F 2/68* | (2006.01) | |
| *A61F 2/64* | (2006.01) | |
| *A61F 2/74* | (2006.01) | |

(52) U.S. Cl.
CPC .................. *A61F 2/68* (2013.01); *A61F 2/64* (2013.01); *A61F 2/80* (2013.01); *A61F 2002/6614* (2013.01); *A61F 2002/742* (2013.01); *A61F 2002/745* (2013.01)

(58) Field of Classification Search
CPC ........ A61F 2/66; A61F 2/80; A61F 2002/802; A61F 2002/807
See application file for complete search history.

(56) References Cited

U.S. PATENT DOCUMENTS

| 708,685 A | 9/1902 | White |
| 980,457 A | 1/1911 | Toles |
| 1,288,803 A | 12/1918 | Beck |
| 1,586,015 A | 5/1926 | Underwood |

(Continued)

FOREIGN PATENT DOCUMENTS

| AU | 670631 B2 | 7/1996 |
| BE | 675 386 A | 5/1966 |

(Continued)

OTHER PUBLICATIONS

International Search Report and Written Opinion from PCT Application No. PCT/US2017/048354, dated Nov. 16, 2017.

(Continued)

*Primary Examiner* — Bruce E Snow
(74) *Attorney, Agent, or Firm* — Workman Nydegger

(57) ABSTRACT

A prosthetic system includes first and second parts rotatable relative to one another about a joint. The first and second parts are adapted to form at least part of a weight bearing connection between a prosthetic foot and a socket. A pump system includes a pump mechanism operatively connected to the first and second parts. Rotation of the first part and/or the second part about the joint moves the pump mechanism between an original configuration in which the volume of a fluid chamber defined by the pump mechanism is zero or near-zero, and an expanded configuration in which the volume of the fluid chamber is increased.

7 Claims, 8 Drawing Sheets

(56) References Cited

U.S. PATENT DOCUMENTS

| | | |
|---|---|---|
| 2,424,278 A | 7/1947 | Kunkel |
| 2,464,443 A | 3/1949 | Ganoe et al. |
| 2,530,285 A | 11/1950 | Catranis |
| 2,533,404 A | 12/1950 | Sharp et al. |
| 2,606,325 A | 8/1952 | Nielson et al. |
| 2,664,572 A | 1/1954 | Blevens |
| 2,671,225 A | 3/1954 | Schoene et al. |
| 2,696,010 A | 12/1954 | Robinson |
| 2,696,011 A | 12/1954 | Galdik |
| 2,790,180 A | 4/1957 | Hauser |
| 2,808,593 A | 10/1957 | Andersen |
| 3,253,600 A | 5/1966 | Scholl |
| 3,322,873 A | 5/1967 | Hitchcock |
| 3,377,416 A | 4/1968 | Kandel |
| 3,557,387 A | 1/1971 | Ohlenbusch et al. |
| 3,631,542 A | 1/1972 | Potter |
| 3,712,298 A | 1/1973 | Snowdon et al. |
| 3,732,578 A | 5/1973 | Pollack |
| 3,751,733 A | 8/1973 | Fletcher et al. |
| 3,806,958 A | 4/1974 | Gusev |
| 3,858,379 A | 1/1975 | Graves et al. |
| 3,889,301 A | 6/1975 | Bonner, Sr. |
| 3,895,405 A | 7/1975 | Edwards |
| 3,922,727 A | 12/1975 | Bianco |
| 3,947,156 A | 3/1976 | Becker |
| 3,975,350 A | 8/1976 | Hudgin et al. |
| 3,991,424 A | 11/1976 | Prahl |
| 4,010,052 A | 3/1977 | Edwards |
| 4,106,745 A | 8/1978 | Carrow |
| 4,133,776 A | 1/1979 | Pruett et al. |
| 4,282,325 A | 8/1981 | Rubenstein et al. |
| 4,283,800 A | 8/1981 | Wilson |
| 4,314,398 A | 2/1982 | Pettersson |
| 4,381,768 A | 5/1983 | Erichsen et al. |
| 4,404,296 A | 9/1983 | Schapel |
| 4,456,642 A | 6/1984 | Burgdorfer et al. |
| 4,466,936 A | 8/1984 | Schapel |
| 4,479,272 A | 10/1984 | Beldzidsky |
| 4,623,354 A | 11/1986 | Childress et al. |
| 4,634,446 A | 1/1987 | Kristinsson |
| 4,635,626 A | 1/1987 | Lerman |
| 4,655,779 A | 4/1987 | Janowiak |
| 4,704,129 A | 11/1987 | Massey |
| 4,822,371 A | 4/1989 | Jolly et al. |
| 4,828,325 A | 5/1989 | Brooks |
| 4,888,829 A | 12/1989 | Kleinerman et al. |
| 4,908,037 A | 3/1990 | Ross |
| 4,923,475 A | 5/1990 | Gosthnian et al. |
| 5,007,937 A | 4/1991 | Fishman et al. |
| 5,108,455 A | 4/1992 | Telikicherla |
| 5,108,456 A | 4/1992 | Coonan, III |
| 5,133,776 A | 7/1992 | Crowder |
| 5,139,523 A | 8/1992 | Paton et al. |
| 5,163,965 A | 11/1992 | Rasmusson et al. |
| 5,201,774 A | 4/1993 | Greene |
| 5,211,667 A | 5/1993 | Danforth |
| 5,221,222 A | 6/1993 | Townes |
| 5,258,037 A | 11/1993 | Caspers |
| 5,314,497 A | 5/1994 | Fay et al. |
| 5,353,525 A | 10/1994 | Grim |
| 5,362,834 A | 11/1994 | Schapel et al. |
| 5,376,129 A | 12/1994 | Faulkner et al. |
| 5,376,131 A | 12/1994 | Lenze et al. |
| 5,376,132 A | 12/1994 | Caspers |
| 5,397,628 A | 3/1995 | Crawley et al. |
| 5,405,407 A | 4/1995 | Kodama et al. |
| 5,480,455 A | 1/1996 | Norvell |
| 5,490,537 A | 2/1996 | Hill |
| 5,507,834 A | 4/1996 | Laghi |
| 5,534,034 A | 7/1996 | Caspers |
| 5,549,709 A | 8/1996 | Caspers |
| 5,555,216 A | 9/1996 | Drouot |
| 5,571,208 A | 11/1996 | Caspers |
| 5,593,454 A | 1/1997 | Helmy |
| 5,658,353 A | 8/1997 | Layton |
| 5,658,354 A | 8/1997 | Norvell |
| 5,702,488 A | 12/1997 | Wood et al. |
| 5,702,489 A | 12/1997 | Slemker |
| 5,709,017 A | 1/1998 | Hill |
| 5,728,166 A | 3/1998 | Slemker |
| 5,728,167 A | 3/1998 | Lohmann |
| 5,728,168 A | 3/1998 | Laghi et al. |
| 5,728,169 A | 3/1998 | Norvell |
| 5,728,170 A | 3/1998 | Becker et al. |
| 5,732,578 A | 3/1998 | Kang |
| 5,735,906 A | 4/1998 | Caspers |
| 5,807,303 A | 9/1998 | Bays |
| 5,830,237 A | 11/1998 | Kania |
| 5,846,063 A | 12/1998 | Lakic |
| 5,885,509 A | 3/1999 | Kristinsson |
| 5,888,216 A | 3/1999 | Haberman |
| 5,888,230 A | 3/1999 | Helmy |
| 5,888,231 A | 3/1999 | Sandvig et al. |
| 5,904,721 A | 5/1999 | Henry et al. |
| 5,904,722 A | 5/1999 | Caspers |
| 5,931,872 A | 8/1999 | Lohmann |
| 5,944,760 A | 8/1999 | Christensen |
| 5,980,577 A | 11/1999 | Radis et al. |
| 5,984,972 A | 11/1999 | Huston et al. |
| 6,007,582 A | 12/1999 | May |
| 6,063,125 A | 5/2000 | Arbogast et al. |
| 6,066,107 A | 5/2000 | Habermeyer |
| D429,335 S | 8/2000 | Caspers et al. |
| 6,117,117 A | 9/2000 | Mauch |
| 6,136,039 A | 10/2000 | Kristinsson et al. |
| 6,149,691 A | 11/2000 | Fay et al. |
| 6,231,616 B1 | 5/2001 | Helmy |
| 6,231,617 B1 | 5/2001 | Fay |
| 6,273,918 B1 | 8/2001 | Yuhasz et al. |
| 6,287,345 B1 | 9/2001 | Slemker et al. |
| 6,296,669 B1 | 10/2001 | Thorn et al. |
| 6,334,876 B1 | 1/2002 | Perkins |
| 6,361,568 B1 | 3/2002 | Hoerner |
| 6,362,387 B1 | 3/2002 | Carlson et al. |
| 6,402,788 B1 | 6/2002 | Wood et al. |
| 6,406,499 B1 | 6/2002 | Kania |
| 6,478,826 B1 | 11/2002 | Phillips et al. |
| 6,485,776 B2 | 11/2002 | Janusson et al. |
| 6,508,842 B1 | 1/2003 | Caspers |
| 6,544,292 B1 | 4/2003 | Laghi |
| 6,554,868 B1 | 4/2003 | Caspers |
| 6,589,289 B2 | 7/2003 | Ingimarsson |
| 6,602,295 B1 | 8/2003 | Doddroe et al. |
| 6,613,096 B1 | 9/2003 | Shirvis |
| 6,626,952 B2 | 9/2003 | Janusson et al. |
| 6,645,253 B2 | 11/2003 | Caspers |
| 6,673,117 B1 | 1/2004 | Soss et al. |
| 6,702,858 B2 | 3/2004 | Christensen |
| 6,706,364 B2 | 3/2004 | Janusson et al. |
| 6,726,726 B2 | 4/2004 | Caspers |
| 6,761,742 B2 | 7/2004 | Caspers |
| 6,767,370 B1 | 7/2004 | Mosler et al. |
| 6,797,008 B1 | 9/2004 | Arbogast et al. |
| 6,855,170 B2 | 2/2005 | Gramnas |
| 6,863,695 B2 | 3/2005 | Doddroe et al. |
| 6,926,742 B2 | 8/2005 | Caspers et al. |
| 6,964,688 B1 | 11/2005 | Kania |
| 6,969,408 B2 | 11/2005 | Lecomte et al. |
| 6,974,484 B2 | 12/2005 | Caspers |
| 7,001,563 B2 | 2/2006 | Janusson et al. |
| 7,025,792 B2 | 4/2006 | Collier |
| 7,025,793 B2 | 4/2006 | Egilsson |
| 7,105,122 B2 | 9/2006 | Karason |
| 7,118,602 B2 | 10/2006 | Bjarnason |
| 7,371,262 B2 | 5/2008 | Lecomte et al. |
| 7,427,297 B2 | 9/2008 | Patterson et al. |
| 7,448,407 B2 | 11/2008 | Alley et al. |
| 7,468,079 B2 | 12/2008 | Collier |
| 7,686,848 B2 | 3/2010 | Christensen |
| 7,744,653 B2 | 6/2010 | Rush et al. |
| 7,909,884 B2 | 3/2011 | Egilsson et al. |
| 7,922,775 B2 | 4/2011 | Caspers |
| 7,947,085 B2 | 5/2011 | Haines et al. |
| 7,993,413 B2 | 8/2011 | Perkins et al. |

(56) References Cited

U.S. PATENT DOCUMENTS

| | | |
|---|---|---|
| 8,007,543 B2 | 8/2011 | Martin |
| 8,034,120 B2 | 10/2011 | Egilsson et al. |
| 8,052,760 B2 | 11/2011 | Egilsson et al. |
| 8,080,065 B2 | 12/2011 | Scussel et al. |
| 8,097,043 B2 | 1/2012 | Egilsson |
| 8,097,766 B2 | 1/2012 | Carlson et al. |
| 8,114,167 B2 | 2/2012 | Caspers |
| 8,298,294 B2 | 10/2012 | Kaltenborn et al. |
| 8,317,876 B2 | 11/2012 | Mosler |
| 8,343,233 B2 | 1/2013 | Perkins et al. |
| 8,523,951 B2 | 9/2013 | Kania |
| 8,894,719 B2 | 11/2014 | Egilsson et al. |
| 8,956,422 B2 | 2/2015 | Halldorsson |
| 8,961,618 B2 | 2/2015 | Lecomte et al. |
| 9,044,348 B2 * | 6/2015 | Halldorsson ............ A61F 2/80 |
| 9,056,022 B2 | 6/2015 | Egilsson et al. |
| 9,066,822 B2 | 6/2015 | Caldwell et al. |
| 9,072,617 B2 | 7/2015 | Halldorsson et al. |
| 9,198,780 B2 | 12/2015 | Jonsson et al. |
| 9,259,332 B2 | 2/2016 | Danzig et al. |
| 9,486,335 B2 | 11/2016 | Halldorsson et al. |
| 9,615,946 B2 | 4/2017 | Halldorsson et al. |
| 9,820,873 B2 | 11/2017 | Sandahl |
| 9,889,025 B2 | 2/2018 | Jonsson et al. |
| 9,943,421 B2 | 4/2018 | Sverrisson et al. |
| 2001/0005798 A1 | 6/2001 | Caspers |
| 2001/0016781 A1 | 8/2001 | Caspers |
| 2002/0052663 A1 | 5/2002 | Herr et al. |
| 2002/0087215 A1 | 7/2002 | Caspers |
| 2002/0091449 A1 | 7/2002 | Caspers et al. |
| 2002/0103545 A1 | 8/2002 | Arbogast et al. |
| 2002/0128580 A1 | 9/2002 | Carlson et al. |
| 2003/0191539 A1 | 10/2003 | Caspers |
| 2004/0024322 A1 | 2/2004 | Caspers |
| 2004/0030411 A1 | 2/2004 | Caspers |
| 2004/0049290 A1 | 3/2004 | Bedard |
| 2004/0064195 A1 | 4/2004 | Herr |
| 2004/0122528 A1 | 6/2004 | Egilsson |
| 2004/0163278 A1 | 8/2004 | Caspers et al. |
| 2004/0181290 A1 | 9/2004 | Caspers |
| 2004/0236434 A1 | 11/2004 | Carstens |
| 2004/0260403 A1 | 12/2004 | Patterson et al. |
| 2005/0131324 A1 | 6/2005 | Bledsoe |
| 2005/0131549 A1 | 6/2005 | Caspers |
| 2005/0143838 A1 | 6/2005 | Collier |
| 2005/0240282 A1 | 10/2005 | Rush et al. |
| 2005/0267603 A1 | 12/2005 | Lecomte et al. |
| 2006/0074493 A1 | 4/2006 | Bisbee, III et al. |
| 2006/0111664 A1 | 5/2006 | Samson et al. |
| 2006/0212130 A1 | 9/2006 | Collier |
| 2006/0212131 A1 | 9/2006 | Curtis |
| 2006/0224246 A1 | 10/2006 | Clausen et al. |
| 2007/0005149 A1 | 1/2007 | Egilsson et al. |
| 2007/0043316 A1 | 2/2007 | Carlson et al. |
| 2007/0050044 A1 | 3/2007 | Haynes et al. |
| 2007/0055383 A1 | 3/2007 | King |
| 2007/0112440 A1 | 5/2007 | Perkins et al. |
| 2007/0196222 A1 | 8/2007 | Mosler et al. |
| 2007/0204487 A1 | 9/2007 | Clough |
| 2007/0213839 A1 | 9/2007 | Nachbar |
| 2008/0086218 A1 | 4/2008 | Egilsson |
| 2008/0147202 A1 | 6/2008 | Danzig et al. |
| 2008/0147204 A1 | 6/2008 | Ezenwa |
| 2008/0243266 A1 | 10/2008 | Haynes et al. |
| 2008/0269911 A1 | 10/2008 | Street et al. |
| 2008/0269912 A1 | 10/2008 | Gobbers et al. |
| 2009/0036998 A1 | 2/2009 | Finlinson et al. |
| 2009/0132056 A1 | 5/2009 | Kania |
| 2009/0157196 A1 | 6/2009 | Danzig et al. |
| 2009/0198346 A1 | 8/2009 | Perkins et al. |
| 2009/0204229 A1 | 8/2009 | Mosler et al. |
| 2009/0281637 A1 | 11/2009 | Martin |
| 2010/0070051 A1 | 3/2010 | Carstens |
| 2010/0087931 A1 | 4/2010 | Bogue |
| 2010/0106260 A1 | 4/2010 | Phillips |
| 2010/0262261 A1 | 10/2010 | Laghi |
| 2010/0312359 A1 | 12/2010 | Caspers |
| 2010/0312360 A1 | 12/2010 | Caspers |
| 2010/0331749 A1 | 12/2010 | Powaser |
| 2011/0035027 A1 | 2/2011 | McCarthy |
| 2011/0046748 A1 | 2/2011 | Martin et al. |
| 2011/0060421 A1 | 3/2011 | Martin et al. |
| 2011/0071649 A1 | 3/2011 | McKinney |
| 2011/0087142 A1 | 4/2011 | Ravikumar et al. |
| 2011/0125291 A1 | 5/2011 | Tompkins et al. |
| 2011/0130846 A1 | 6/2011 | Kampas et al. |
| 2011/0184532 A1 | 7/2011 | Tompkins |
| 2011/0202143 A1 | 8/2011 | Caspers |
| 2011/0270413 A1 | 11/2011 | Haynes |
| 2011/0295386 A1 | 12/2011 | Perkins et al. |
| 2012/0000092 A1 | 1/2012 | Ingvarsson et al. |
| 2012/0022667 A1 | 1/2012 | Accinni et al. |
| 2012/0035520 A1 | 2/2012 | Ingimudarson et al. |
| 2012/0123559 A1 | 5/2012 | Mosler et al. |
| 2012/0173000 A1 | 7/2012 | Caspers |
| 2012/0173001 A1 | 7/2012 | Caspers |
| 2012/0191217 A1 | 7/2012 | Mackenzie |
| 2013/0053982 A1 | 2/2013 | Halldorsson |
| 2013/0096694 A1 | 4/2013 | Caldwell et al. |
| 2013/0211544 A1 | 8/2013 | Jonsson et al. |
| 2013/0282142 A1 | 10/2013 | Perkins et al. |
| 2013/0289741 A1 | 10/2013 | Halldorsson et al. |
| 2014/0243997 A1 | 8/2014 | Clausen et al. |
| 2014/0249648 A1 | 9/2014 | Sandahl |
| 2016/0000585 A1 | 1/2016 | Sandahl |
| 2016/0120665 A1 | 5/2016 | Muller |
| 2016/0199202 A1 | 7/2016 | Jonasson et al. |
| 2016/0338859 A1 * | 11/2016 | Sverrisson ............ F04B 45/04 |
| 2016/0346100 A1 | 12/2016 | Sverrisson et al. |
| 2017/0056210 A1 | 3/2017 | Jonasson et al. |
| 2017/0181871 A1 | 6/2017 | Halldorsson et al. |
| 2018/0008436 A1 | 1/2018 | Sandahl |

FOREIGN PATENT DOCUMENTS

| | | |
|---|---|---|
| CA | 2 098 945 C | 7/1997 |
| CN | 1946358 A | 4/2007 |
| CN | 1989342 A | 6/2007 |
| CN | 101815870 A | 8/2010 |
| DE | 685 861 C | 12/1939 |
| DE | 745 981 C | 5/1944 |
| DE | 27 12 342 A1 | 9/1977 |
| DE | 27 29 800 A1 | 1/1979 |
| DE | 32 21 920 A1 | 4/1983 |
| DE | 42 17 877 A1 | 12/1992 |
| DE | 43 21 182 C1 | 12/1994 |
| DE | 94 18 210 U1 | 1/1995 |
| DE | 94 19 211 U1 | 2/1995 |
| DE | 94 17 913 U1 | 3/1995 |
| DE | 299 05 020 U1 | 7/1999 |
| DE | 29823435 U1 | 7/1999 |
| EP | 0 019 612 A1 | 11/1980 |
| EP | 0 057 838 A1 | 8/1982 |
| EP | 0 057 839 A1 | 8/1982 |
| EP | 0 086 147 A1 | 8/1983 |
| EP | 0 261 884 A1 | 3/1988 |
| EP | 0 320 170 A1 | 6/1989 |
| EP | 0 363 654 A2 | 4/1990 |
| EP | 0 631 765 A1 | 1/1995 |
| EP | 0 650 708 A1 | 5/1995 |
| EP | 0 870 485 A2 | 10/1998 |
| EP | 1 509 176 A1 | 3/2005 |
| EP | 1 875 881 A1 | 1/2008 |
| EP | 2816978 A1 | 12/2014 |
| FR | 1 135 516 A | 4/1957 |
| FR | 1 532 625 A | 7/1968 |
| FR | 2 420 035 A1 | 10/1979 |
| FR | 2 501 999 A1 | 9/1982 |
| GB | 136 504 A | 12/1919 |
| GB | 267 988 A | 3/1927 |
| GB | 2 069 847 A | 9/1981 |
| GB | 2 149 309 A | 6/1985 |
| JP | H07-155343 A | 6/1995 |
| SE | 88-01686 A | 3/1989 |

(56) References Cited

FOREIGN PATENT DOCUMENTS

| | | |
|---|---|---|
| SU | 1667855 A1 | 8/1991 |
| SU | 1771722 C | 10/1992 |
| SU | 1812982 A3 | 4/1993 |
| SU | 1821177 A1 | 6/1993 |
| WO | 84/00881 A1 | 3/1984 |
| WO | 95/05792 A1 | 3/1995 |
| WO | 96/21405 A1 | 7/1996 |
| WO | 98/04218 A1 | 2/1998 |
| WO | 98/55055 A1 | 12/1998 |
| WO | 99/05991 A2 | 2/1999 |
| WO | 99/65434 A1 | 12/1999 |
| WO | 00/03665 A1 | 1/2000 |
| WO | 00/74611 A2 | 12/2000 |
| WO | 01/54631 A1 | 8/2001 |
| WO | 01/70147 A2 | 9/2001 |
| WO | 02/26158 A2 | 4/2002 |
| WO | 02/065958 A2 | 8/2002 |
| WO | 02/067825 A2 | 9/2002 |
| WO | 02/080813 A2 | 10/2002 |
| WO | 03/077797 A2 | 9/2003 |
| WO | 03/099173 A1 | 12/2003 |
| WO | 03/099188 A1 | 12/2003 |
| WO | 2005/039444 A2 | 5/2005 |
| WO | 2005/105000 A1 | 11/2005 |
| WO | 2006012820 A1 | 2/2006 |
| WO | 2010/141960 A2 | 12/2010 |
| WO | 2011/035099 A1 | 3/2011 |
| WO | 2012010309 A1 | 1/2012 |
| WO | 2012177965 A1 | 12/2012 |
| WO | 2014126554 A1 | 8/2014 |
| WO | 2014194998 A1 | 12/2014 |
| WO | 2016112030 A1 | 7/2016 |

OTHER PUBLICATIONS

Brochure, "Sometimes Less is More, Harmony P3" Otto Bock, 12 pages. Available at, http://www.ottobock.com/cps/rde/xbcr/ob_es/646A303-EN-01-1001w.pdf, dated 2012.

Information Guide, "Harmony Users Guide Otto Bock, 9 pages, available at http://media.ottobock.com/Prosthetics/Socket-Technologies/Harmony/_Genreal/Files/12072403.1_OB-Harmony-UsersGuide-9-10-12.pdf", dated 2012.

Brochure,"Harmony Certification Course Manual, " Original Harmony Pump, 42 pages. Availiable at, http://academy.ottobockus.com/videos/harmony/data/downloads/harmony%20course%20manual%202013.pdf. Dated 2013.

Brochure, Harmony P2 & HD, 2 pages. Available at http://www.ottobock.com/cps/rde/xchg/ob_us_en/hs.xsl/14904.html?id=4641. Dated 2012.

Haberman, Louis J., "Silicone-Only Suspension (SOS) with Socket-Loc and the Ring for the Lower Limb", found at, http://www.oandp.org/jpo/library/1995_01_002.asp. Journal of Prosthetics and Orthotics 1995; vol. 7, No. 1, p. 2, 19 pages, dated 2012.

* cited by examiner

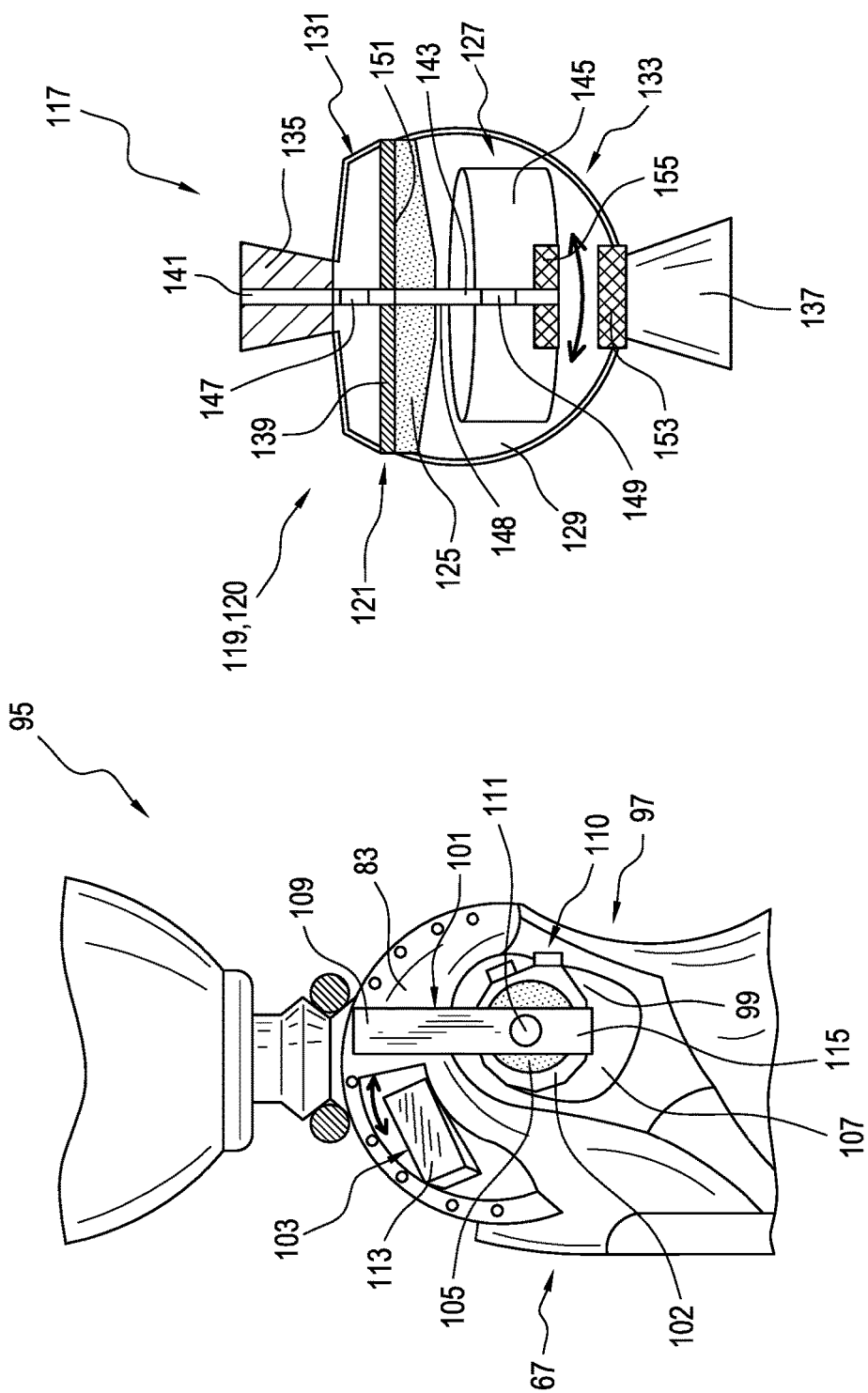

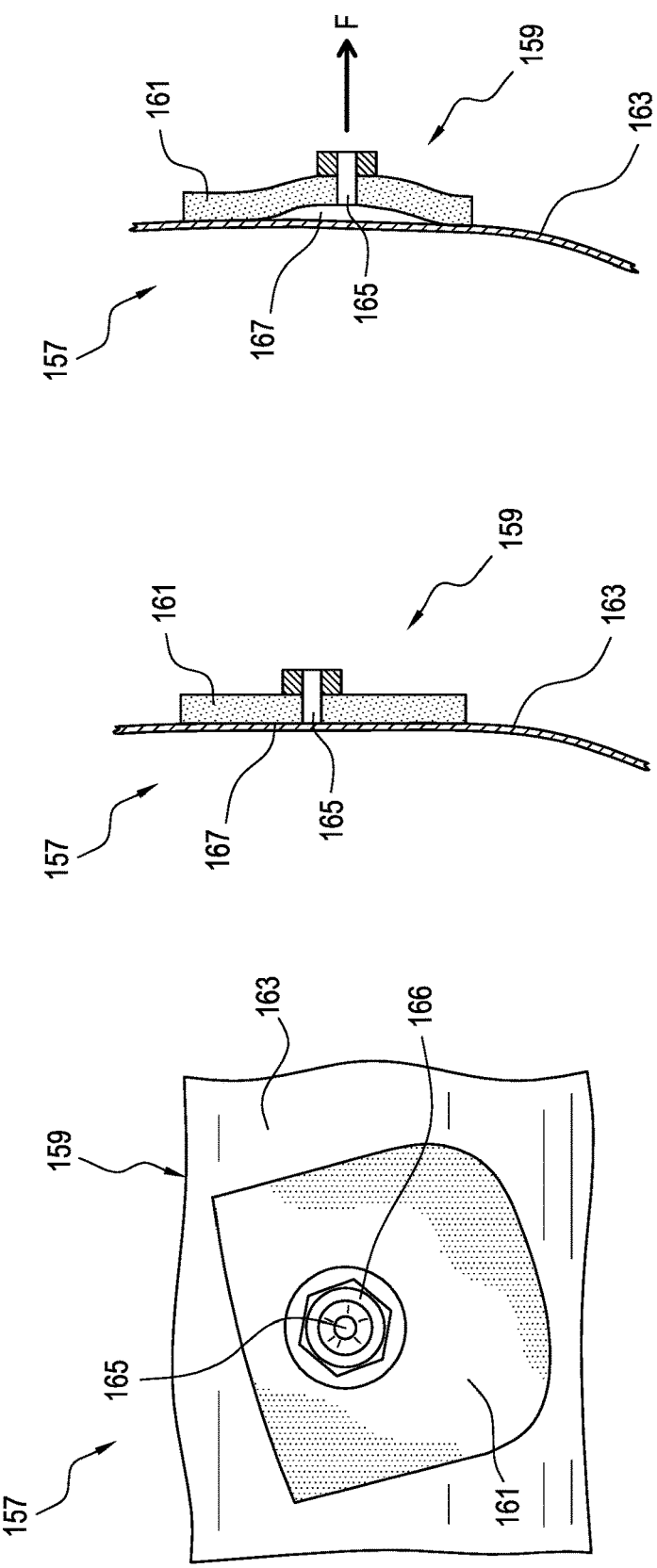

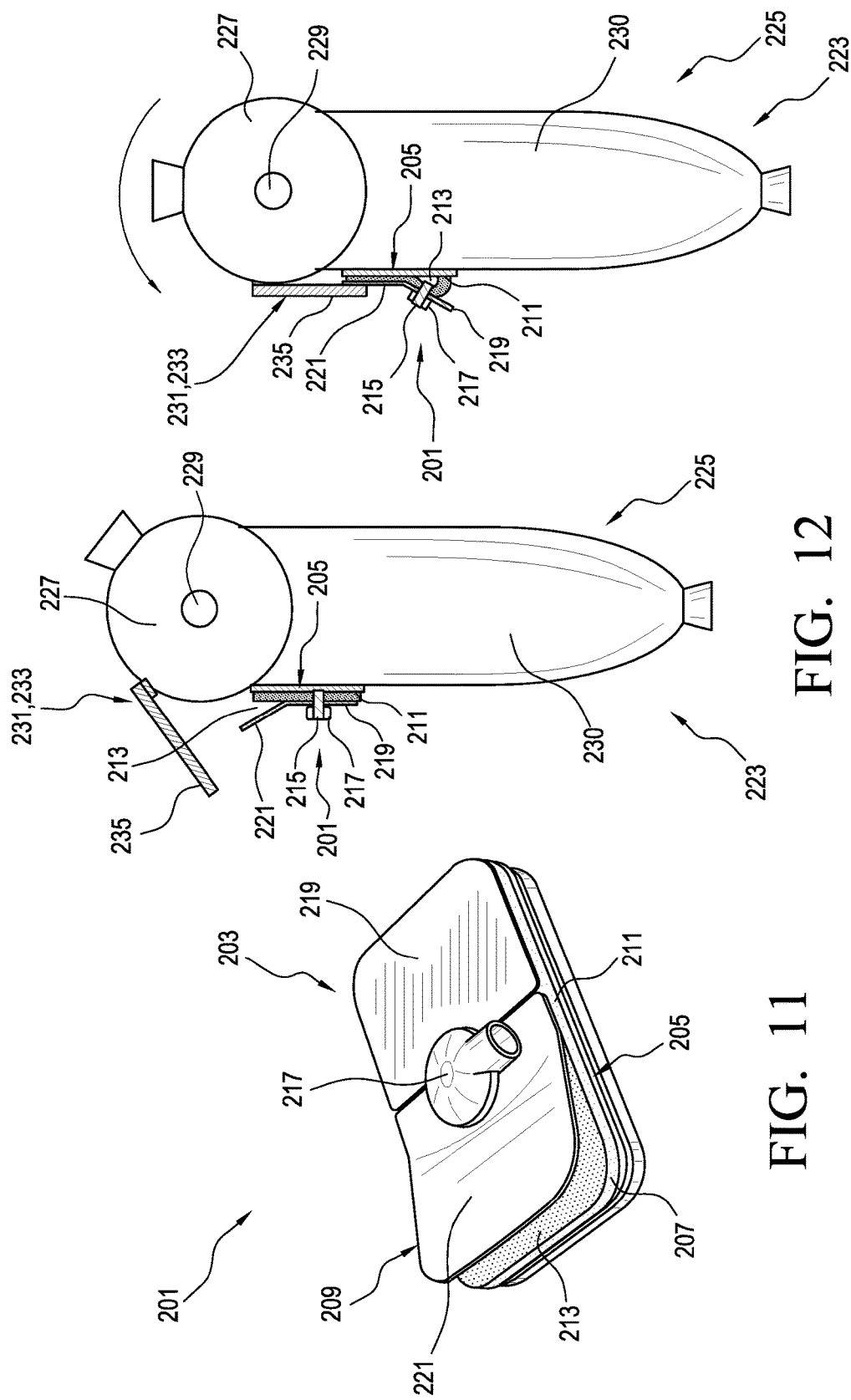

PUMP SYSTEM

TECHNICAL FIELD

The disclosure relates to the field of prosthetic devices, and more particularly to a prosthetic device, system and pump mechanism for increasing vacuum in a vacuum assisted suspension system.

BACKGROUND

An ongoing challenge in the development of prosthetic devices is the attachment of the prosthetic device to the residual limb of a user. For prosthetic legs, it is often difficult to securely attach the prosthetic leg to the residual leg without exerting too much or uneven pressure on the residual limb. On the one hand, the lack of a secure attachment can adversely affect the user's ability to walk. On the other hand, an improper fit can cause sores, swelling and pain for the user.

One approach for overcoming this challenge has been the application of a negative pressure vacuum in a space between the limb (or a liner donned on the limb) and a socket or receptacle coupled to the prosthetic limb. Two conventional ways to apply such a vacuum are by a mechanical pump or an electronic pump.

Mechanical pumps are often in-line systems that utilize the movement of the user to generate the negative pressure vacuum in the socket. For example, the force generated by contacting the ground during a user's walking motion can be used to generate a vacuum in the socket space to hold the prosthesis to the user's limb. However, in utilizing the motion of the user, known pumps rely on complete compression of the pump to expel air from the pump before the pump can be decompressed to generate the vacuum. Because the impact and displacement of the pump is not consistent and varies between users, the vacuum and thus attachment between the residual limb and the socket can be unpredictable and/or inadequate, causing the user discomfort, grief and even injury. Many of such pumps are also bulky and significantly contribute to the weight of the prosthetic limb, imposing a significant weight burden on the user when walking.

There is a need for a prosthetic device, system, and pump mechanism that provides freedom of vacuum suspension for a prosthetic system. There is also a call for a prosthetic device that provides a secure vacuum without losing suction and confidence to the user over a period of time. It is also desirable for prosthetic devices to draw a vacuum while being lightweight and streamlined.

SUMMARY

Embodiments of the prosthetic system provide vacuum assisted suspension by generating negative pressure inside a prosthetic socket worn over a residual limb, and reducing sliding movement between the liner and the socket. The prosthetic system of the present disclosure advantageously can produce a vacuum effect in a prosthetic socket utilizing a pivoting, swinging, or rotating mechanism at a joint rather than relying primarily on a force or pressure applied to the prosthetic system by the user.

According to an embodiment, the prosthetic system includes first and second parts rotatable relative to one another about a joint. The first and second parts form at least part of a weight bearing connection between a prosthetic foot and a socket. A pump system includes a pump mechanism operatively connected to the first and second parts.

Relative rotation between the first and second parts about the joint moves the pump mechanism between an original configuration in which the volume of a fluid chamber defined by the pump mechanism is zero or near-zero, and an expanded configuration in which the volume of the fluid chamber is increased. For instance, during weight bearing or when a load is applied to the prosthetic system, a support member of the pump system flexes or bends, which, in turn, causes a movable member of the pump system to pivot or rotate about the joint and toward the second part.

When the movable member rotates about the joint toward the second part, the movable member rotates away from the support member, which, in turn, moves the pump mechanism toward the expanded configuration, pulling fluid into the pump mechanism. After weight bearing or when the load is removed, stored energy in the support member forces the first and second parts to rotate away from one another. This moves the movable member and the pump mechanism back toward the original configuration, expelling fluid out of the pump mechanism.

The pump system can thus generate a vacuum in a socket using a pivoting or rotating movement between the first and second parts. Further, it can do so without undesirably affecting the functionality of a prosthetic knee or foot associated with the prosthetic system or significantly increasing the bulk of the system. According to a variation, the pump system can be located at or near the socket such that there is no need to move fluid drawn into the pump mechanism from the socket all the way down the prosthetic foot. This advantageously reduces the time required to produce an elevated vacuum in the socket. Further, it eliminates or reduces the need of a long tube extending between the prosthetic foot and the socket, reducing the likelihood of leaks and volume to generate vacuum.

According to a variation, the pump mechanism can be incorporated into a prosthetic knee. For instance, the first part can comprise a rotatable part of the prosthetic knee.

BRIEF DESCRIPTION OF THE DRAWINGS

These and other features, aspects, and advantages of the present disclosure will become better understood regarding the following description, appended claims, and accompanying drawings.

FIG. 4 shows a side view of a prosthetic system according to another embodiment.

FIG. 5 shows a side view of a prosthetic system according to another embodiment.

FIG. 6 shows a top view of a prosthetic system according to another embodiment.

FIG. 7 shows a side view of the prosthetic system in FIG. 6.

FIG. 8 shows another side view of the prosthetic system in FIG. 6.

FIG. 11 shows a perspective view of a pump system according to another embodiment.

FIG. 12 shows a side view of a prosthetic system including the pump system in FIG. 11 according to an embodiment.

FIG. 13 shows another side view of the prosthetic system in FIG. 12.

DETAILED DESCRIPTION OF THE DISCLOSURE

Figure 1A:
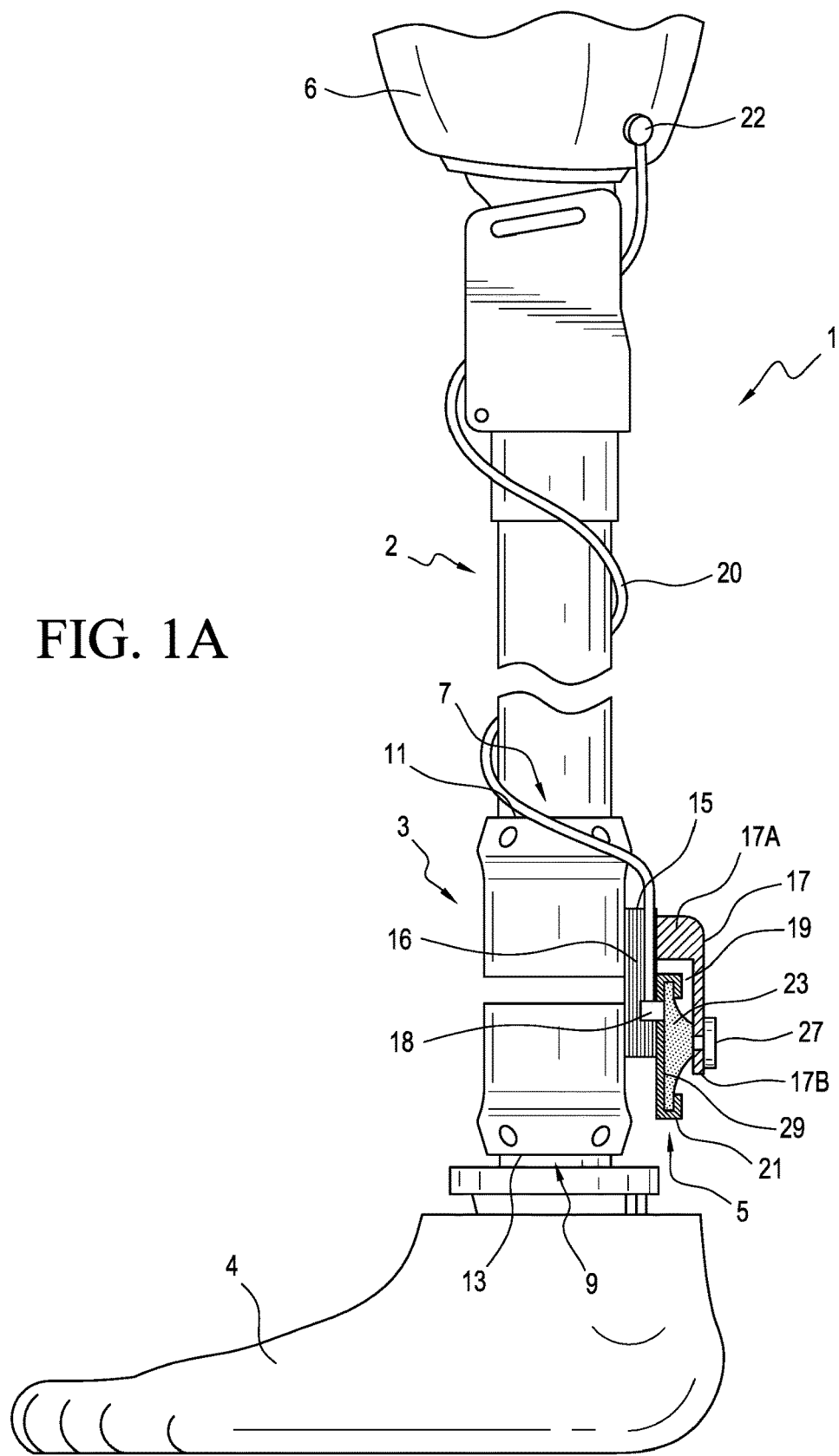
FIG. 1A shows a side view of a prosthetic system according to an embodiment.

It will be understood that, unless a term is expressly defined in this disclosure to possess a described meaning, there is no intent to limit the meaning of such term, either expressly or indirectly, beyond its plain or ordinary meaning.

Any element in a claim that does not explicitly state "means for" performing a specified function, or "step for" performing a specific function, is not to be interpreted as a "means" or "step" clause as specified in 35 U.S.C. § 112, paragraph 6.

The embodiments of a prosthetic system will be described which form part of a vacuum system. A vacuum pump system having a fluid connection with a socket assists in creating a vacuum between a residual limb and the socket by pumping fluid out of the socket. The fluid can be pumped out of the socket manually or in swing and/or stance. For instance, pivotal movement about a joint between a socket and a pylon of the prosthetic system can cause a pump mechanism of the present disclosure to increase the volume of a fluid chamber in the pump mechanism. The increase in volume of the pump mechanism draws in fluid from the vacuum space between the residual limb and the socket of a prosthetic system. In this manner, the pump mechanism decreases the air pressure within the vacuum space causing a vacuum effect.

The volume of the fluid chamber in the pump mechanism can also automatically decrease. The connection between the vacuum space and the pump mechanism may have a one-way valve assembly, so all of the air within the volume of the pump mechanism is expelled out of an outlet to another space or to atmosphere. The outlet can be provided with a one-way valve assembly so the vacuum space is the only source of air.

The prosthetic system of the present disclosure advantageously can produce a vacuum effect in a prosthetic socket utilizing a pivoting, swinging, or rotating mechanism at a joint rather than relying primarily on a force or pressure applied to the prosthetic system by the user. The prosthetic system of the present disclosure also produces a vacuum effect that is advantageous over prior art devices that require compression of the pump to expel air before the pump can be decompressed to draw in air. The present disclosure achieves smaller fluctuations in air pressure than the prior art systems, so the difference between the greatest pressure and lowest pressure in the vacuum space of the socket is less.

The pump mechanism embodiments may easily retrofit on existing prosthetic devices and can do so without undesirably affecting their function. They are also lightweight and low-profile, advantageously contributing little to no bulk to a prosthetic foot. Optionally, the pump mechanism embodiments can be located at or near the socket such that there is no need to move fluid drawn into the pump mechanism from the socket down to the prosthetic foot. This advantageously reduces the time required to produce an elevated vacuum in the socket. Further, it eliminates or reduces the need of a long tube extending between the prosthetic foot and the socket, reducing the likelihood of leaks and volume to generate vacuum.

The efficiency of the pump mechanism is determined at least in part by how effectively the volume of the fluid chamber is reduced. Since the pump mechanism begins at and returns to the original state of zero or near-zero volume, the volume of the fluid chamber is determined by the pivoting force applied to the pump, not by a full compression and recompression cycle as in the prior art. In addition, all fluid drawn into the pump mechanism is expelled afterwards, fully utilizing the volume of the fluid chamber.

The vacuum suspension system also reduces volume fluctuations of the residual limb and allows for increased proprioception and reduced pistoning since there is a better attachment between the socket and the residual limb. It may also be beneficial to produce hypobaric pressure below a certain level in the socket. This may be achieved using a sealing membrane or seal component between the residual limb and the socket, instead of the conventional sealing method of using a sleeve to form an airtight connection between the residual limb and the proximal end of the socket. The sealing membrane may be on a prosthetic liner as described in U.S. Pat. Nos. 8,034,120, 8,894,719, and 9,056,022, all incorporated by reference and belonging to the assignee of this disclosure.

The benefit of using a liner having a seal or seal component reduces the volume of air to be drawn out of the socket and therefore, a better suspension may be achieved in a shorter time period. Using a silicone liner with integrated seal also provides the added benefit that the hypobaric region is not directly applied to the skin.

The vacuum pump mechanisms in the embodiments of the prosthetic system described are generally described as a pump system or mechanism and may include any suitable type of pump mechanism. For instance, the pump mechanism may be a pump as described in U.S. Pat. Nos. 9,072,617, 9,044,348, 9,486,335, and 9,615,946 and U.S. patent application Ser. Nos. 14/747,788 and 15/457,266, all incorporated by reference and belonging to the assignee of this disclosure. A piston-type pump may be used in the embodiments in place of a membrane-type pump. A bladder-type pump may also be used in the embodiments in place of a membrane-type pump, and a skilled person would understand that the pump mechanisms described may also be used with a bladder-type pump and vice versa.

A bladder-type pump has an interior fluid chamber surrounded by an airtight material. When the interior chamber is expanded, the opposing walls are moved away from each other by extending at least one side wall of the pump. The side walls of the bladder-type pump may have an accordion-like shape or be formed of a polymeric material which allow for the increase in distance between the opposing walls.

A membrane-type pump has at least one wall of flexible material and a second opposing wall which may be rigid or flexible. The edges of the two walls are attached to each other such that when a force applies to the pump to expand the interior fluid chamber, the force deforms at least the flexible wall, and the flexible wall arcs outward to form an interior fluid chamber. To allow for deformation, the flexible wall may be made of a polymeric material including elastomeric material such as rubber or plastic.

The bladder-type pump and membrane-type pump are arranged so that the initial volume of the interior fluid chamber is zero or near-zero. The pumps described and shown have a cylindrical shape. A skilled person would understand that the pumps may have a variety of shapes, for example, a diamond, rectangular, or triangular shape.

The specific embodiments of the prosthetic device will now be described regarding the figures.

Figure 1B:
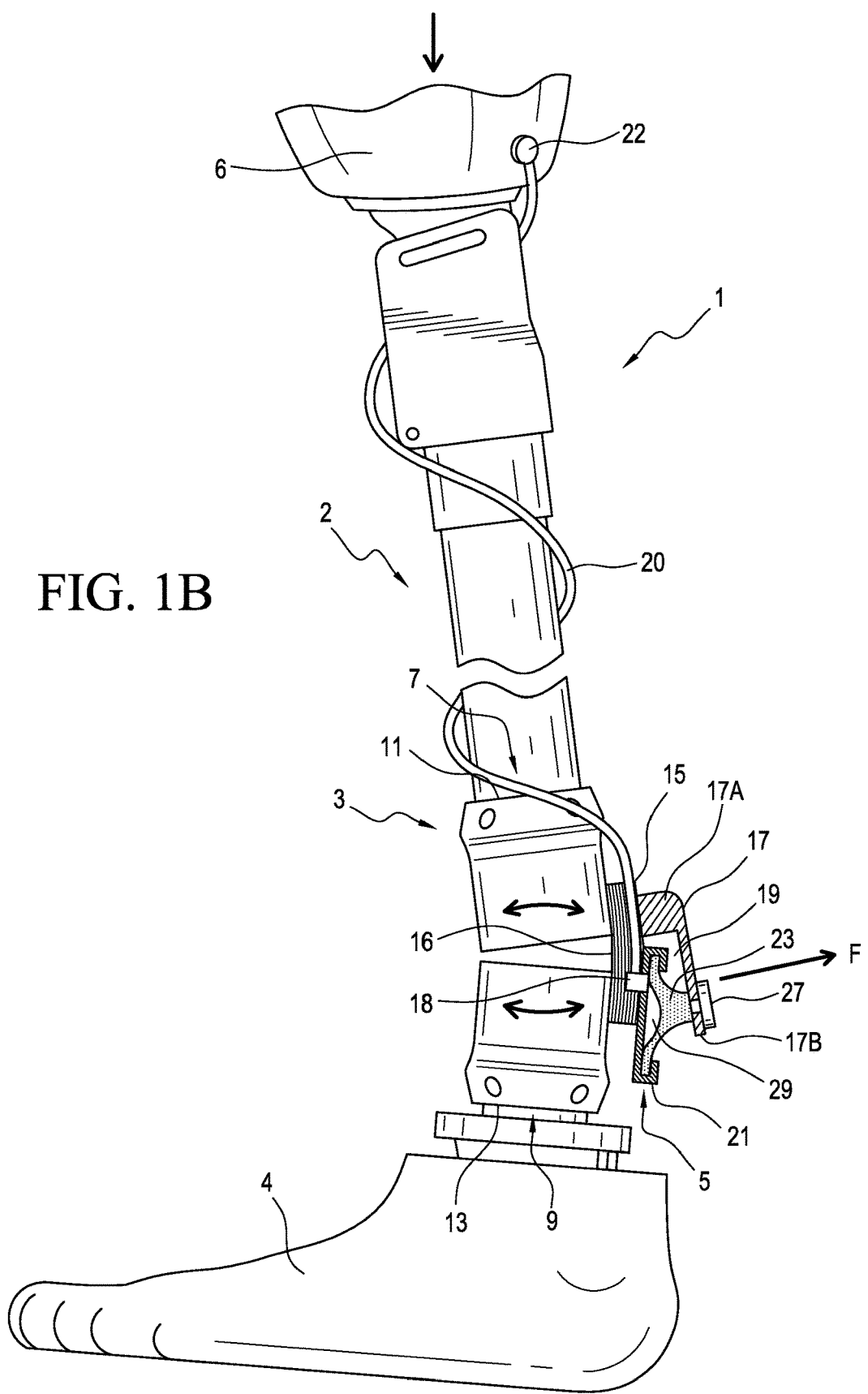
FIG. 1B shows another side view of the prosthetic system in FIG. 1A.

FIGS. 1A and 1B show a prosthetic system 1 including a pump system 3. As seen in FIG. 1A, the pump system 3 comprises a prosthetic connector having a pump mechanism 5, an upper section 7, and a lower section 9. The prosthetic connector is arranged to form at least part of a weight bearing connection 2 between a prosthetic foot 4 and a socket 6 as shown. A tube 20 and valve 22 can connect the pump mechanism 5 to the socket 6.

At least one of the upper and lower sections 7, 9 is arranged to rotate or move relative to the other. In an embodiment, the upper section 7 includes an attachment adaptor 11 and the lower section 9 includes an attachment adaptor 13. The adaptors 11, 13 are shown as female adaptors but can be male adaptors or any other suitable attachment adaptors.

A support member 15 connects the upper section 7 and the lower section 9. The support member 15 has load-carrying configuration and defines a joint 16 about which at least one of the upper and lower sections 7, 9 pivots relative to the other. When no load is placed on the prosthetic system 1, the support member 15 maintains its shape and supports the upper section 7 and the lower section 9 a distance from one another. When a load is placed on the prosthetic system 1, the support member 15 flexes or bends, which, in turn, pivots the upper and lower sections 7, 9 relative to one another about the joint 16. The joint 16 can be located anywhere along the length of the support member 15. The support member 15 can be made of polymer material, carbon fiber, metal, combinations thereof, or any other suitable material.

The pump mechanism 5 is positioned in a receiving space 19 defined between the support member 15 and the movable member 17. The pump mechanism 5 includes a housing 21 attached to the support member 15 and a membrane 23 operatively connected to a movable member 17. The pump mechanism 5 may include at least one valve assembly 18 arranged to control movement of fluid into and from the pump mechanism 5.

The pump mechanism 5 relies upon deformation of the membrane 23 to move between an original configuration (shown in FIG. 1A) in which the volume of a fluid chamber 29 defined between the membrane 23 and the housing 21 is zero or near-zero, and an expanded configuration (shown in FIG. 1B) in which the volume of the fluid chamber 29 is increased.

When a force F is exerted on the membrane 23 in a direction away from the housing 21, the pump mechanism 5 moves toward the expanded configuration (shown in FIG. 1B) as the force pulls the center portion of the membrane 23 away from the housing 21, causing deformation of the membrane 23 and an increase in volume of the fluid chamber 29. This increase in volume of the fluid chamber 29 can draw fluid into the fluid chamber 29 from the socket 6 through at least one valve assembly 18. The housing 21 may be formed of metal such as stainless steel, carbon fiber, or plastic or any other material which would provide sufficient strength to resist deformation when pulled away from the membrane 23.

Once the force F is removed from the membrane 23, the pump mechanism 5 returns toward its original configuration (shown in FIG. 1A) as the membrane 23 returns toward the housing 21 and fluid within the fluid chamber 29 is expelled out of the at least one valve assembly. The membrane 23 can be elastomeric and can use at least in part its material properties to naturally or elastically return to its original position on the housing 21.

The membrane 23 may have any desired shape but is shown having a generally elliptical or circular shape. The membrane 23 can be attached at or near its center point to the movable member 17 via a connector 27 while the outer radial edge portion of the membrane 23 is attached to the housing 21. When the membrane 23 is pulled away from the housing 21, a pocket forms in the middle area of the membrane 23 due to the deformation of the membrane 23. The formation of the pocket increases the volume of the fluid chamber 29. The pump mechanism 5 thus uses a compliant membrane to create suction. The connecter 27 can be an insert formed of metal, plastic, or any other suitable material. In other embodiments, the connector 27 may be formed of a material that is part of the membrane 23.

The movable member 17 has a rigid configuration and is connected to the support member 15. The movable member 17 can include a base part 17A and an elongated part 17B. The base part 17A can be attached to a proximal portion of the support member 15 and extends a distance outwardly therefrom. The elongated part 17B extends generally downward from the base part 17A and is connected to the membrane 23 via the connector 27.

The movable member 17 can define an opening or slot for receiving the connector 27. To attach the movable member 17 to the membrane 23, a shaft portion of the connector 27 can be received in the opening or slot such that the elongated part 17B of the movable member 17 is connected to the connector 27. The connector 27 can be attached to the movable member 17 via a pin, nut, flange, removable head portion, or other fastener. Through the structure of the connector 27 and the movable member 17, the pump mechanism 5 has the benefit of being easily and quickly removed and/or replaced from prosthetic system 1.

During weight bearing or when a load is applied to the prosthetic system 1, the support member 15 flexes or bends, which, in turn, causes the upper section 7 and the base part 17A of the movable member 17 to pivot or rotate about the joint 16 and toward the lower section 9 as seen in FIG. 1A.

When the base part 17A rotates about the joint 16 toward the lower section 9, the elongated part 17B of the movable member 17 rotates away from the support member 15, which, in turn, causes the connector 27 to pull the membrane 23 away from the housing 21, increasing the volume of the fluid chamber 29. This increase in volume of the fluid chamber 29 creates a vacuum in the pump mechanism 5, pulling fluid into the pump mechanism 5. Pivoting movement between the upper and lower sections 7, 9 thus automatically creates a vacuum in the pump mechanism 5.

After weight bearing or when the load is removed, stored energy in the support member 15 forces the upper and lower sections 9, 11 to rotate away from one another. This moves the elongated part 17B of the movable member 17 back toward the housing 21, moving the membrane 23 toward the housing 21 and expelling fluid within the fluid chamber 29 out of the pump mechanism 5. As such, the support member 15 can both move the pump mechanism 5 toward the expanded configuration when loaded, and bias the pump mechanism 5 from the expanded configuration toward the original configuration when unloaded.

The pump system 3 can thus generate a vacuum in a socket using a pivoting or swinging movement between the upper and lower sections 9, 11 without undesirably affecting the functionality of a prosthetic foot associated with the system or significantly increasing the bulk of the prosthetic system 1.

The pump system 3 is shown being located closer to the foot 4 than the socket 6 but it will be appreciated that the pump system 3 can be located at any suitable position within the system 1. For instance, the pump system 3 can be located nearer to the socket 6 such that there is no need to move fluid drawn into the pump mechanism from the socket 6 down to the prosthetic foot 4. This advantageously reduces the time required to produce an elevated vacuum in the socket. Further, it eliminates or reduces the need of a long tube extending between the prosthetic foot and the socket, reducing the likelihood of leaks and volume to generate vacuum.

Figure 2:
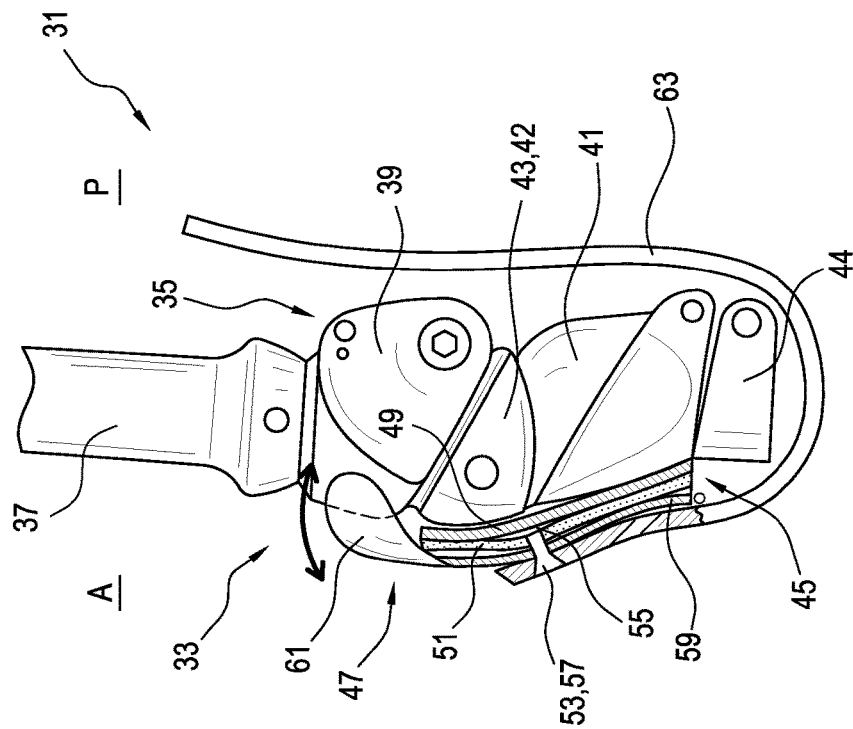
FIG. 2 shows a side view of a prosthetic system according to another embodiment.

FIG. 2 illustrates a prosthetic system 31 including a pump system 33 according to another embodiment. The system 31 includes a prosthetic knee 35 and a pylon 37 connected to the prosthetic knee 35. The prosthetic knee 35 can be any suitable prosthetic knee and is arranged to form at least part of a weight bearing connection between a prosthetic foot and a socket.

In order to better understand the operation of the system 31, a basic discussion of the gait cycle is provided. A gait cycle defines the movement of the leg between successive heel contacts of the same foot. The gait cycle has two phases: stance and swing. The stance phase has three time periods: heel-strike, mid-stance and toe-off. During mid-stance, the knee joint will be at full extension. Maximum flexion of the knee joint, while walking, will occur at the end of the toe-off phase. Immediately following the end of the toe-off phase begins the swing phase.

While the stance phase has three time periods, the swing phase has two time periods: acceleration and deceleration. The acceleration phase begins immediately following the maximum flexion during the toe-off phase. During the acceleration phase, the lower portion of the leg, comprising the shin and foot, swings back towards full extension. In a natural knee joint, a deceleration phase follows the acceleration phase, during which the lower portion of the leg continues to swing towards full extension.

The knee 35 includes a proximal part 39, a distal part 41, and a link 43 connecting the proximal part 39 and the distal part 41. According to a variation, the link 43 can comprise a load-dependent brake system 43 arranged to selectively prevent rotation of the proximal part 39 relative to the distal part 41 when the knee 35 is loaded by a user in stance. When the load on the knee 35 is removed or reduced, the load-dependent brake system can be released and the knee 35 can swing or the proximal part 39 can rotate relative to the distal part 41 about a joint 42 defined by the link 43. The pylon 27 can be attached to an attachment adaptor positioned at the top of the proximal part 39 and a distal tube clamp attachment 44.

The pump system 33 includes a pump mechanism 45 and a movable member 47. The pump mechanism 45 includes a housing 49, a membrane 51, and at least one valve assembly 53 arranged to control movement of fluid into and from the pump mechanism 45. The housing 49 comprises a base plate attached to the anterior portion of the distal part 41.

The pump mechanism 45 relies upon deformation of the membrane 51 to move between an original configuration in which the volume of a fluid chamber 55 defined between the membrane 51 and the housing 49 is zero or near-zero, and an expanded configuration (shown in FIG. 2) in which the volume of the fluid chamber 55 is increased. The membrane 51 may have any desired shape.

The membrane 49 can be attached at or near its center point to the movable member 47 via a connector 57 while the outer radial edge portion of the membrane 51 can be attached to the housing 49. When the membrane 51 is pulled away from the housing 49, a pocket forms in the middle area of the membrane 51 due to the deformation of the membrane 51. The formation of the pocket increases the volume of the fluid chamber 55, creating suction. The connector 57 can be made of any suitable material. In an embodiment, the connector 57 can define a through channel in fluid communication with the fluid chamber 55 and the at least one valve assembly 53.

The movable member 47 has a rigid configuration and is located on the anterior portion of the knee 35 and spans the proximal part 39 and the distal part 41. The movable member 47 can define an opening or slot for receiving the connector 57. Through the structure of the connector 57 and the movable member 47, the pump system 33 has the benefit of being easily and quickly removed and/or replaced from the system 31. The movable member 47 includes a distal end portion 59 arranged to engage the distal part 41 of the knee 35 and a proximal end portion 61 arranged to engage the distal part 39 of the knee 35. The distal end portion 59 of the movable member 47 can be pivotally connected to the knee 35 at or near a distal region thereof.

At extension of the knee 35, the proximal end portion 61 engages the proximal part 39 as the proximal part 39 rotates in a counterclockwise direction about the joint 42. This pushes the movable member 47 away from the housing 49 and causes the connector 57 to pull the membrane 51 away from the housing 49, increasing the volume of the fluid chamber 55. This increase in volume of the fluid chamber 55 creates a vacuum in the pump mechanism 45, pulling fluid into the pump mechanism 45 through a tube 63 attached to the socket.

During flexion of the knee 35, the proximal end portion 61 disengages the proximal part 39 as the proximal part 39 rotate about the joint 42 to decrease the angle therebetween, which, in turn, allows the pump mechanism 45 to return toward its original configuration. As the membrane 51 returns toward the housing 49, fluid within the fluid chamber 55 is expelled out of the at least one valve assembly 53. As noted above, the membrane 51 can be elastomeric and can use at least in part its material properties to naturally or elastically return to its original position on the housing 49. Optionally, the pump mechanism 45 can include a closure-assist mechanism arranged to bias or move the pump mechanism 45 toward its original configuration and/or maintain it therein.

The pump system 33 can thus generate a vacuum using the swinging or pivoting movement of the knee 35 without undesirably affecting the functionality of the knee or significantly increasing the bulk of the prosthetic system 31. In addition, the pump mechanism 45 can be located nearer to the socket such that there is no need to move fluid drawn into the pump mechanism from the socket down to a prosthetic foot. This advantageously reduces the time required to produce an elevated vacuum in the socket. Further, it eliminates or reduces the need of a longer tube extending between the prosthetic foot and the socket, reducing the likelihood of leaks and volume to generate vacuum. While the pump system is shown positioned on the anterior of the knee, it will be appreciated that the pump system can be positioned at any suitable position on a knee.

Figure 3:
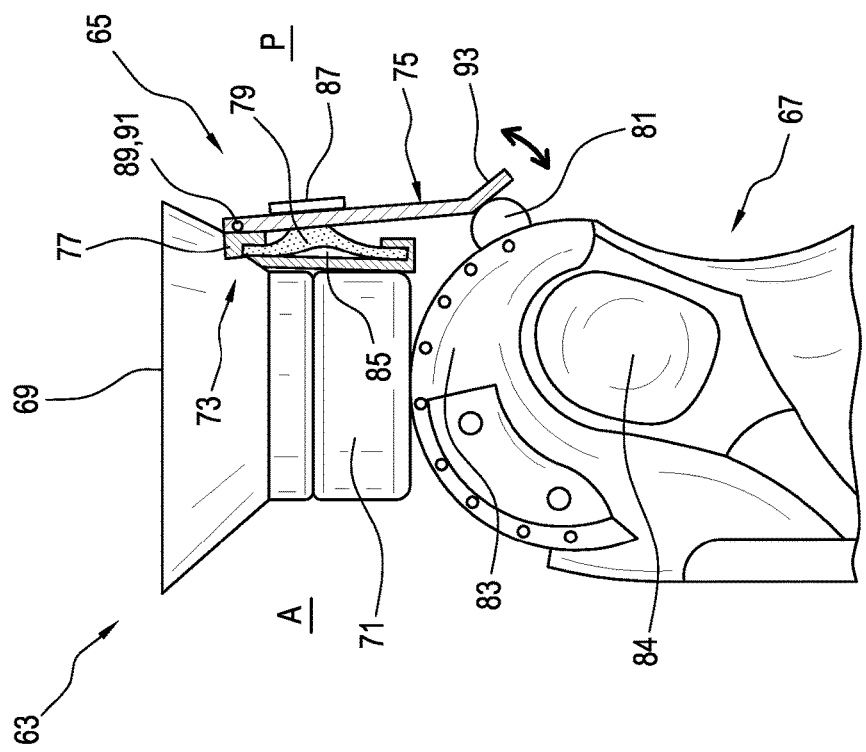
FIG. 3 shows a side view of a prosthetic system according to another embodiment.

FIG. 3 illustrates yet another embodiment of a pump system located on a posterior aspect of a prosthetic knee. As shown, a prosthetic system 63 including a pump system 65 is positioned on a posterior aspect P of a prosthetic knee 67. The system 63 includes a socket assembly 69 arranged to embrace a residual limb and the prosthetic knee 67 connected to the socket assembly 69. The socket assembly 69 can be attached to an attachment adaptor 71 positioned at the top the knee 67. The knee 67 defines a joint 84 and a first part 83 arranged to rotate about the joint 84. The knee 67 is arranged to form at least part of a weight bearing connection between a prosthetic foot and the socket assembly 69.

The pump system 65 includes a pump mechanism 73, a movable member 75, and a protrusion 81 on the first part 83 of the knee 67. The pump mechanism 73 includes a housing 77, a membrane 79, and at least one valve assembly arranged to control movement of fluid into and/or from the pump mechanism 73. The housing 77 is attached to the posterior aspect P of the attachment adaptor 71.

The pump mechanism 73 relies upon deformation of the membrane 79 to move between an original configuration in which the volume of a fluid chamber 85 defined between the membrane 79 and the housing 77 is zero or near-zero, and an expanded configuration (shown in FIG. 3) in which the volume of the fluid chamber 85 is increased. The membrane 79 may have any desired shape.

The membrane 79 can be attached at or near its center point to the movable member 75 while the outer radial edge portion of the membrane 79 can be attached to the housing 77. The membrane 79 can be attached to the movable member 75 via a connecter 87. The connector 87 can be made of any suitable material. In an embodiment, the connector 87 can define a through channel in fluid communication with the fluid chamber 85 and the at least one valve assembly.

The movable member 75 has a rigid configuration and includes a proximal end portion 89 attached to the housing 77 at a first location point 91. In the illustrated embodiment, the movable member 75 can be pivotally attached to the housing 77 at the first location point 91. In other embodiments, the movable member 75 can be arranged to flex or bend at or near the first location point 91. The movable member 75 can be integral to the housing 77.

The movable member 75 includes a distal end portion 93 arranged to selectively engage the protrusion 81 on the first part 83 of the knee 67. The protrusion 81 can have any suitable shape but is shown having a rounded or curved outer surface. The protrusion 81 can be attached to the first part 83 of the knee 67. The protrusion 81 can be integral to the first part 83. The protrusion is arranged to selectively lift the movable member 75 away from the housing 77 by engaging the distal end portion 93 of the movable member 75.

At extension of the knee 67, the protrusion 81 on the first part 83 of the knee 76 engages the distal end portion 93 of the movable member 75 as the first part 83 straightens relative to the socket assembly 69, which, in turn, lifts or rotates the movable member 75 away from the housing 77. This causes the connector 87 to pull the membrane 79 away from the housing 77, increasing the volume of the fluid chamber 85. This increase in volume of the fluid chamber 85 creates a vacuum in the pump mechanism 73.

During flexion of the knee 67, the protrusion 81 disengages the distal end portion 93 of the movable member 75, which, in turn, allows the pump mechanism 73 to return toward its original configuration. As the membrane 79 returns toward the housing 77, fluid within the fluid chamber 85 is expelled out of the pump mechanism 73. According to a variation, the movable member 75 can be arranged to bias the pump mechanism 73 toward its original configuration.

Similar to the previous embodiment, the pump system 65 can thus generate a vacuum using the swinging or pivoting movement of the knee 67 without undesirably affecting the functionality of the knee or significantly increasing the bulk of the prosthetic system 63. In addition, the pump mechanism 73 can be located nearer to the socket assembly 69 such that there is no need to move fluid drawn into the pump mechanism 73 from the socket system 69 down to a prosthetic foot.

FIG. 4 illustrates a prosthetic system 95 including a pump system 97 according to another embodiment. The prosthetic system 95 is similar in structure and function to the prosthetic system 63 except that the pump system is located on a side of the prosthetic knee. For instance, the pump system 97 includes a pump mechanism 99, a movable member 101, and a protrusion or ramp member 103 on the first part 83 of the knee 67.

The pump mechanism 99 includes a housing 102, a membrane 105, and at least one valve assembly 110 arranged to control movement of fluid into and/or from the pump mechanism 99. The housing 102 is attached to a second part 107 of the knee 67 that is rotatable relative to the first part 83.

Similar to the previously described embodiments, the pump mechanism 99 relies upon deformation of the membrane 105 to move between an original configuration in which the volume of a fluid chamber defined between the membrane 105 and the housing 103 is zero or near-zero, and an expanded configuration in which the volume of the fluid chamber is increased.

The membrane 105 can be attached at or near its center point to the movable member 101 while the outer radial edge portion of the membrane 105 can be attached to the housing 103. The membrane 105 can be attached to the movable member 101 via a connector 111.

The movable member 101 has a rigid or semi-rigid configuration and includes a distal end portion 115 connected to the housing 103. The movable member 101 has an elongate configuration that extends from the distal end portion 115 toward a proximal end portion 109. The movable member 101 can be integral to the housing 103. The movable member 101 can be cantilevered from the housing 101 with the proximal end portion 109 spaced a distance from a side surface of the first part 83.

The proximal end portion 109 is arranged to selectively engage and slide along the protrusion 103 on the first part 83 of the knee 67. The protrusion 103 can have a ramp shape including an inclined contact surface 113 arranged to lift the proximal end portion 109 of the movable member 101 away from the housing 103 as it slides up the protrusion 103.

Upon flexion of the knee 67, the proximal end portion 109 engages and slides up the contact surface 113 of the protrusion 103, which, in turn, lifts or rotates the movable member 101 away from the housing 103. This causes the connector 111 to pull the membrane 99 away from the housing 103, increasing the volume of the fluid chamber.

At extension of the knee 67, the proximal end portion 109 and the protrusion 103 disengage, which, in turn, allows the pump mechanism 99 to return toward its original configuration. As the membrane 105 returns toward the housing 105, fluid within the fluid chamber is expelled out of the at least one valve assembly 107. Optionally, the movable member 101 can be arranged to bias the pump mechanism 99 toward its original configuration. The pump system 97 can thus advantageously generate a vacuum using flexion of the knee 67.

It will be appreciated that locating the pump mechanism 99 where it can be easily reached by a user's hand allows the pump mechanism 99 to be manually activated by the user rather than automatically by the prosthetic knee. For instance, by positioning the pump mechanism 99 on the side of the knee 67 and manipulating the movable member 101, a user can generate and maintain a vacuum pressure in a socket. In other embodiments, embodiments of the pump mechanism can be located on a socket itself and manually operated by a user.

FIG. 5 illustrates a prosthetic system 117 including a pump system 119 according to an embodiment. The pump system 119 comprises a prosthetic connector 120 defining a cavity 129 and including an upper section 131 and a lower section 133. As seen, the upper section 131 can include an attachment adaptor 135 and the lower section 133 can include an attachment adaptor 137. The adaptors 135, 137 are shown as male adaptors but can be female adaptors or any other type of attachment adaptors. It will be appreciated that the prosthetic connector 120 is arranged to form at least part of a weight bearing connection between a prosthetic foot and a socket.

A pump mechanism 121 is located in the cavity 129. The pump mechanism 121 includes a plate member 139, a membrane 125, and a pendulum type mechanism 127. An outer radial edge portion of the membrane 125 can be attached to the plate member 139. A center portion of the membrane 125 can be attached to the pendulum type mechanism 127. For instance, the pendulum type mechanism 127 can comprise a pivoting weighted member 145 suspended from a pivot at or near the center portion of the membrane 125 via an elongated member 148 so that it can swing freely.

A first fluid passageway 141 extends through the upper section 131 and the plate member 139 and a second fluid passageway 143 extends through the membrane 125 and the pendulum type mechanism 127. The pump mechanism 121 can include a first valve assembly 147 positioned in the first passageway 141 that is arranged to control movement of fluid into the pump mechanism 121. A second valve assembly 149 can be positioned in the second fluid passageway 143 to control movement of the fluid out of the pump mechanism 121.

The pump mechanism 121 relies upon deformation of the membrane 125 to move between an original configuration (shown in FIG. 5) in which the volume of a fluid chamber 151 defined between the membrane 125 and the plate member 139 is zero or near-zero, and an expanded configuration in which the volume of the fluid chamber 151 is increased.

In an embodiment, swinging or pivoting movement of the weighted member 145 from a neutral position (shown in FIG. 5) during gait can move the pump mechanism between the original and expanded configurations. For instance, during flexion, the weighted member 145 can swing back and/or forth from the neutral position and the momentum of the weighted member 145 can exert a dynamic tensile force on the membrane 125 to move the pump mechanism between the original and expanded configuration. In other embodiments, the weighted member 145 can swing in unrestricted 360 directions relative to the neutral position. This pulls the membrane 125 away from the plate member 139, increasing the volume of the fluid chamber 151. The increase in volume of the fluid chamber 151 creates a vacuum in the pump mechanism 121, pulling fluid into the pump mechanism 121 through the first valve assembly 147.

At extension, the weighted member 145 can swing back toward the neutral position, which, in turn, allows the pump mechanism 121 to return toward its original configuration. As the membrane 125 returns toward the plate member 139, fluid within the fluid chamber 151 is expelled out of the pump mechanism 121 via the second valve assembly 149.

According to a variation, the pump system 119 can include a closure-assist mechanism arranged to bias the pump mechanism 121 toward the original configuration. For instance, a first magnet 153 can be located on a bottom of the cavity 127 and a corresponding second magnet or ferromagnetic member 155 can be located at the base of the weighted member 145. Magnetic forces between the first and second magnets 153, 155 can function to bring the weighted member 145 back toward the neutral position. While the closure-assist mechanism is described comprising a plurality of magnets, in other embodiments, the closure-assist mechanism can comprise a resilient spring member.

The pump system 119 can thus advantageously draw a vacuum through random or gait motion of the prosthetic system 117, making the pump system 117 more efficient and versatile. Further, the pump system 117 can be placed anywhere near or around the socket or a prosthetic knee.

FIGS. 6-8 show a pump system 157 according to yet another embodiment. The pump system 157 includes a suction cup type pump mechanism. Embodiments of the suction cup type pump mechanism can be adapted to a variety of prosthetic components and to prosthetic feet that are particularly difficult to operate with conventional pump mechanisms, providing versatility.

The pump system 157 comprises a pump mechanism 159 having a suction cup type configuration. The pump mechanism 159 includes an elastomer membrane 161 arranged to be positioned on a sealing surface 163. The sealing surface 163 can comprise an outer surface of a socket, a foot plate, or any other suitable sealing surface. As such, the membrane 161 of the pump mechanism 159 can advantageously be sealed on a variety of prosthetic components and prosthetic feet provided that such components and feet can provide the sealing surface 163.

The membrane 161 is arranged to form a seal with the sealing surface 163. In other words, when there is less pressure in a fluid chamber 167 defined between a bottom of the membrane 161 and the sealing surface 163 than on the outer side of the membrane 161, the pressure differential pushes the membrane 161 down against the sealing surface 163, forcing fluid out and stopping fluid from entering under the edges of the membrane 161 into the fluid chamber 167.

Similar to the other embodiments, the pump mechanism 159 relies upon deformation of the membrane 161 to move between an original configuration in which the volume of the fluid chamber 167 is zero or near-zero, and an expanded configuration in which the volume of the fluid chamber is increased. The membrane 161 can have any suitable shape. For instance, the bottom of the membrane 161 can define a concave curvature.

The membrane 161 defines a passageway 165 in fluid communication with the fluid chamber 167. The passageway 165 can include a fitting 166 arranged to be attached to a tube. According to a variation, a valve assembly can be integrated with the tube or the passageway 165 that is arranged to only allow fluid to enter the fluid chamber 167 via the passageway 165. The valve assembly can comprise a duck-bill valve.

With the membrane 161 sealed on the sealing surface 163, the application of back and forth movement to the membrane 161 can move the pump mechanism 159 between the expanded and original configurations. For instance, when no force is exerted on a center portion of the membrane 161 to expand the fluid chamber 167, the volume of the fluid chamber 167 is zero or near-zero as seen in FIG. 7. When a force F is exerted on the center portion of the membrane 161 to expand the fluid chamber 167, the volume of the fluid chamber 167 is increased, moving the pump mechanism 159 toward the expanded configuration as seen in FIG. 8.

The pump system 157 can thus advantageously create a vacuum using simple and/or random motion to function. The pump system 157 advantageously also does not require a separate mechanism or structure to operate the membrane 161 to create a vacuum in a socket.

According to a variation, as the pump mechanism 159 moves from the expanded configuration toward the original configuration, pressure within the fluid chamber 167 increases until the seal between the membrane 161 and the sealing surface 163 is broken, allowing fluid in the fluid chamber 167 to escape or be expelled out under the sides of the membrane 161. The pump mechanism 159 thus does not require an outlet valve assembly, reducing the overall weight and profile of the pump system 157.

Figure 9:
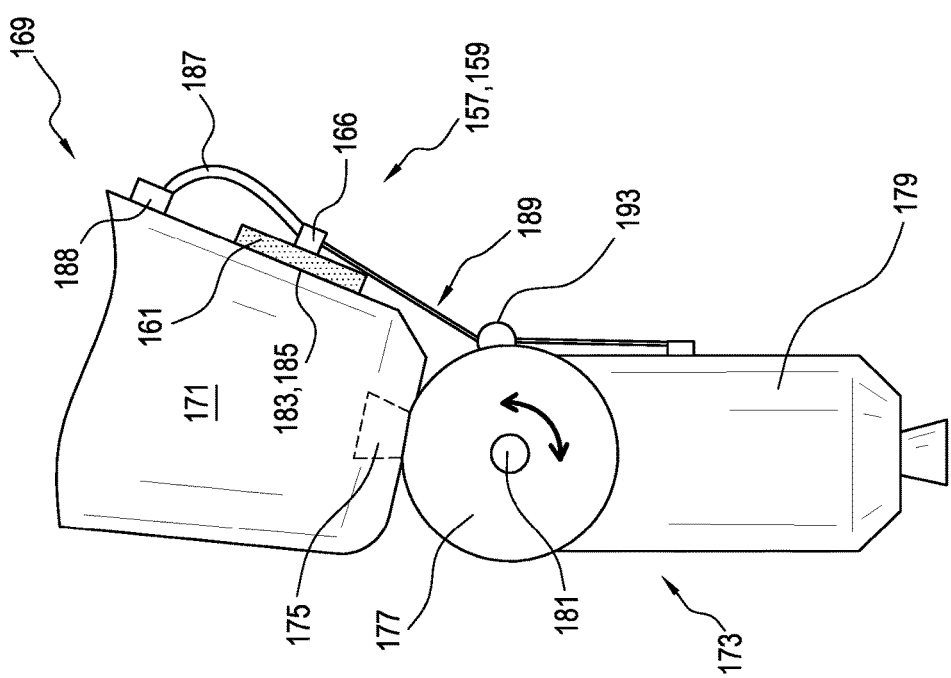
FIG. 9 shows a side view of a prosthetic system including the pump system in FIG. 6 according to an embodiment.

FIG. 9 illustrates a prosthetic system 169 including the pump system 157 according to an embodiment. The prosthetic system 169 includes a socket assembly 171 arranged to receive a residual limb and a prosthetic knee 173 connected to the socket assembly 171. The socket assembly 171 can be attached to an attachment adaptor 175 positioned at the top of the knee 173. The knee 173 includes a proximal part 177 and a distal part 179 attached to the proximal part 177. The proximal part 177 and the socket system 171 are arranged to rotate relative to one another about a joint 181 defined by the knee 173. It will be appreciated that the knee 173 is arranged to form at least part of a weight bearing connection between a prosthetic foot and a socket.

The membrane 161 of the pump mechanism 159 is sealed or placed on a sealing surface 183 defined by an outer surface 185 on the posterior aspect P of the socket assembly 171. A tube 187 connects the pump mechanism 159 to the socket assembly 171 via a valve assembly 188 that is attached to an aperture defined in the socket assembly 171. The tube 187 can be threadedly attached to the threaded fitting 166 of the membrane 161.

A movable member 189 comprising a transfer element operatively connects the pump mechanism 159 to the distal part 179 of the knee 173. The transfer element 189 can be a cable, a lace, a wire or any other suitable member and may refer to a relatively long and relatively thin shaped member and may include a friction reducing coating. The transfer element 189 may be made of any type of material which would provide the transfer element 189 with some rigidity and stiffness including metal, plastic, or fiberglass. The transfer element 189 translates action of the knee 173 to the pump mechanism 159.

According to a variation, the prosthetic system 169 can include a tensioning control mechanism to adjust the length of the transfer element 189. In an embodiment, the transfer element 189 may be placed within a tubular casing. The tubular casing may be made of a variety of materials including plastic or an elastomeric material.

A first end of the transfer element 189 is attached to the pump mechanism 159. The first end of the transfer element 189 can be attached to the threaded fitting 166. From the pump mechanism 159, the transfer element 189 passes through an anchor point 193 on the proximal part 177 of the knee 173 which directs the transfer element 189 downwardly toward the distal part 179 of the knee 173. At the distal part 179 of the knee 173, a second end of the transfer element 189 is attached to the posterior aspect P of the distal part 179.

When the prosthetic system 169 is in flexion, there is slack in the transfer element 189 and the pump mechanism 159 is in its original configuration. As the prosthetic system 169 moves from flexion toward extension, the distal part 179 of the knee 173 rotates about the joint 181 away from the socket system 171. This causes the transfer element 189 to tighten and apply a pulling force on the pump mechanism 159.

The pulling force on the pump mechanism 159 causes the membrane 161 to pull away from the sealing surface 183, moving the pump mechanism 159 to the expanded configuration. More particularly, the transfer element 189 pulls the membrane 161 away from the sealing surface 183 on the socket assembly 171, increasing the volume of the fluid chamber defined between the membrane 161 and the sealing surface 183. This increase in volume of the fluid chamber creates a vacuum in the pump mechanism 159, pulling fluid into the pump mechanism 159 through the tube 187.

As the prosthetic system 169 moves from extension to flexion, the transfer element 189 loosens and the pump mechanism 159 can move back toward its original configuration and decreases the volume of the fluid chamber to zero or near zero. According to a variation, the transfer element 189 has a rigidity and stiffness such that movement from extension to flexion causes the transfer element 189 to slide inside of the tubular casing and exert a pushing force on the membrane 16, pushing the membrane 161 back toward the sealing surface 183.

During the return of the membrane 161 toward the sealing surface 183, the increased pressure in the fluid chamber can break the seal between the membrane 161 and the sealing surface 183, allowing fluid in the fluid chamber to be expelled out under the membrane 161. Because the pump mechanism 159 returns to its original configuration of zero or near-zero volume in the fluid chamber at the beginning or end of each gait cycle, substantially all fluid drawn into the pump mechanism 159 is automatically expelled.

The prosthetic system 169 can thus advantageously use the swinging or pivoting movement between the socket assembly 171 and the distal part 179 of the prosthetic knee 173 to automatically generate a vacuum in the socket assembly 171. In addition, because the pump mechanism 159 is attached directly to the socket assembly 171, the user can easily activate the pump mechanism 159 manually.

Figure 10:
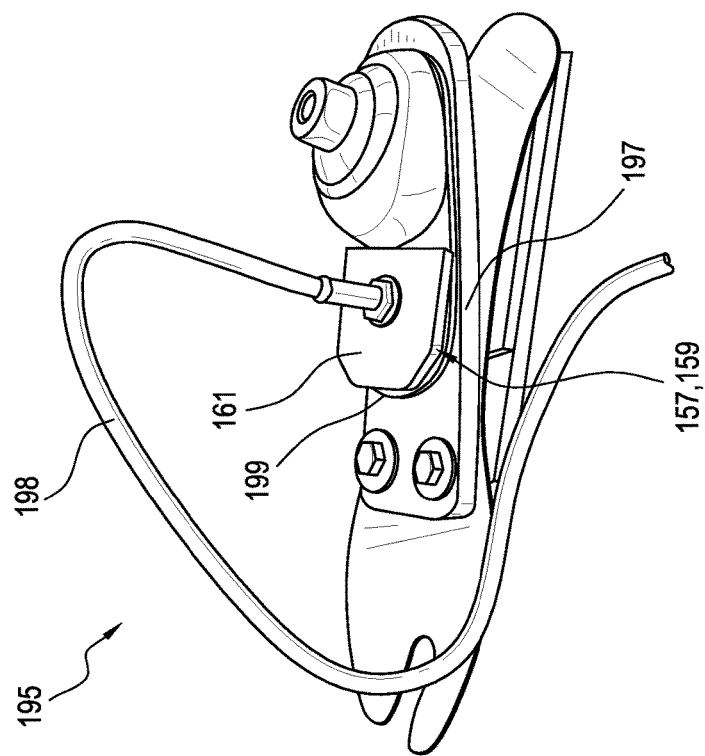
FIG. 10 shows a perspective view of a prosthetic system including the pump system in FIG. 6 according to another embodiment.

FIG. 10 shows yet another embodiment of the pump system 157 implemented with a prosthetic foot. As seen, a prosthetic system 195 can include a prosthetic foot 197 and the pump system 157 secured directly to the foot 197. A tube 198 can fluidly connect the pump system 157 to a prosthetic socket. The membrane 161 of the pump mechanism 159 can be sealed or placed on a sealing surface 199 defined by a proximal surface of the foot 197, providing a sleek and low-profile design.

During gait, the random and/or simple movement between the sealing surface 199 on the foot 197 and the membrane 161 can advantageously create a vacuum in a socket and expel fluid drawn out of the socket to atmosphere while contributing little to no bulk to the foot 197. The pump system 157 can be secured to the foot 197 so that there is a reduced likelihood of the pump system 157 undesirably affecting the functionality of the foot 197, providing a more natural gait.

FIGS. 11-13 show another embodiment of a pump system 201 having a suction cup type configuration adaptable to fit a variety of prosthetic components. Additionally, the pump system 201 can use swinging movement at a joint to activate the pump system 201 rather than using the user's weight applied to the prosthetic component.

As seen, the pump system 201 can include a pump mechanism 203 comprising a base plate 205, a membrane 207, and a top plate 209. The membrane 207 defines a bottom arranged to be sealed or placed on a sealing surface 211 defined by the base plate 205.

The pump mechanism 203 relies upon deformation of the membrane 207 to move between an original configuration in which the volume of a fluid chamber 213 (best seen in FIG. 13) defined between the bottom of the membrane 207 and the sealing surface 211 is zero or near-zero, and an expanded configuration in which the volume of the fluid chamber 213 is increased. The membrane 207 can have any suitable shape but is shown having a shape generally corresponding to the base plate 205.

The membrane 207 defines a passageway 215 in fluid communication with the fluid chamber 213. The pump mechanism 203 can include a fitting 217 in fluid communication with the passageway 215 and arranged to be attached to a tube. Optionally, a valve assembly can be integrated with the fitting 217 or a tube associated with the fitting 217. The valve assembly can be arranged to only allow fluid to enter the fluid chamber 213 via the passageway 215.

According to a variation, as the pump mechanism 203 moves from the expanded configuration toward the original configuration, pressure within the fluid chamber 213 increases until the seal between the membrane 207 and the sealing surface 211 is broken, allowing fluid in the fluid chamber 213 to escape out under the sides of the membrane 207.

The top plate 209 has an angled configuration including a first part 219 connected to center portion of the top of the membrane 207 and a second part 221 angled relative to the first part 219 and extending toward a free end. A variable clearance 213 is defined between the bottom of the second part 221 and the top of the membrane 207. In other embodiments, the top plate 209 can have a curved configuration, a linear configuration, an angled configuration, or combinations thereof.

The top plate 209 is arranged to move the pump mechanism 203 between the original and expanded configurations by rocking back and forth relative to the base plate 205.

With the first part 219 of the top plate 209 generally parallel to the base plate 205 and the second part 221 angled upwardly from the first part 219, the pump mechanism 203 is in the original configuration (shown in FIG. 11). Rotation of the second part 221 toward the base plate 205 decreases the clearance 213 and rotates the first part 219 away from the base plate 205, which, in turn, pulls a center portion of the membrane 207 away from the sealing surface 211. Pulling the center portion of the membrane 207 away from the sealing surface 211 deforms the membrane 207, moving the pump mechanism 205 toward the expanded configuration.

When the second part 221 rotates away from the base plate 205 (increasing the clearance 213) and the first part 219 rotates toward the base plate 205, the pump mechanism 203 returns toward its original configuration (shown in FIG. 11) as the membrane 207 returns toward the sealing surface 211.

The membrane 207 can use at least in part its material properties to naturally or elastically return to its original position on the sealing surface 211.

FIGS. 12 and 13 illustrates a prosthetic system 223 including the pump system 201 according to an embodiment. As seen, the pump system 201 is attached to an anterior aspect of a prosthetic knee 225. The knee 225 includes a proximal part 227 and a distal part 229 attached to the proximal part 227. The proximal part 227 and the distal part 229 are arranged to relative to one another about a joint 230 defined by the knee 225. It will be appreciated that the knee 225 is arranged to form at least part of a weight bearing connection between a prosthetic foot and a socket.

A movable member 231 comprising an arm 233 is attached to the proximal part 227 of the knee 225. The arm 233 has an elongate configuration and extends generally downward from the outer surface of the proximal part 227. The arm 233 defines a distal portion 235 arranged to selectively engage the second part 221 of the top plate. The arm 233 may be made of any type of material which would provide the arm 233 with rigidity and stiffness including metal, plastic, carbon fiber, or the like. The arm 233 translates swinging or pivoting action of the knee 225 to the pump mechanism 203.

When the knee 225 is in flexion, the distal portion 235 of the arm 233 is separated or spaced a distance from the second part 221 of the top plate 209 and the pump mechanism 203 is in its original configuration as seen in FIG. 12.

As the knee 225 moves from flexion toward extension as seen in FIG. 13, the distal portion 235 of the arm 233 engages and applies direct pressure or force on the second part 221 of the top plate 209 of the pump mechanism 205. The applied pressure or force causes the second part 221 of the top plate 209 to rotate toward the base plate 205 and the first part 219 of the top plate 209 to rotate away from the base plate 205, moving the pump mechanism 203 to the expanded configuration. In an embodiment, the first part 219 of the top plate 209 pulls a center portion of the membrane 207 away from the sealing surface 211, increasing the volume of the fluid chamber 213. This increase in volume of the fluid chamber 213 creates a vacuum in the pump mechanism 205, pulling fluid into the fluid chamber 213 through the passageway 215.

As the knee 225 moves from extension and flexion, the distal portion 235 of the arm 233 disengages from the first part 219 of the top plate 209 and the pump mechanism 203 can move back toward its original configuration. During the return of the membrane 207 toward the sealing surface 211, the increased pressure in the fluid chamber 213 can break the seal between the membrane 207 and the sealing surface 211, allowing fluid in the fluid chamber 213 to be expelled out under the membrane 207. Because of the pump mechanism 203 returns to its original configuration of zero or near-zero volume in the fluid chamber at the beginning or end of each gait cycle, substantially all fluid drawn into the pump mechanism 203 is automatically expelled.

The prosthetic system 223 can thus beneficially use the swinging or pivoting movement of the knee 225 to automatically generate a vacuum in a socket or socket assembly. The pump mechanism 203 is located near the socket such that there is no need to move fluid drawn into the pump mechanism 203 from the socket to a prosthetic foot. This beneficially reduces the time required to produce an elevated vacuum in the socket. It also eliminates or reduces the need of a long tube extending between the prosthetic foot and the socket, reducing the likelihood of leaks and volume to generate vacuum.

Figure 15:
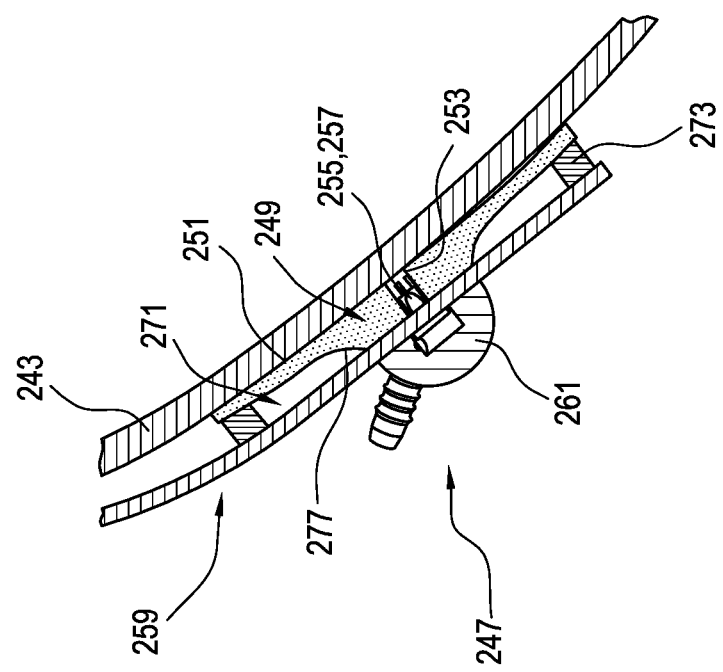
FIG. 15 shows a cross section view of the prosthetic system in FIG. 14.
Figure 14:
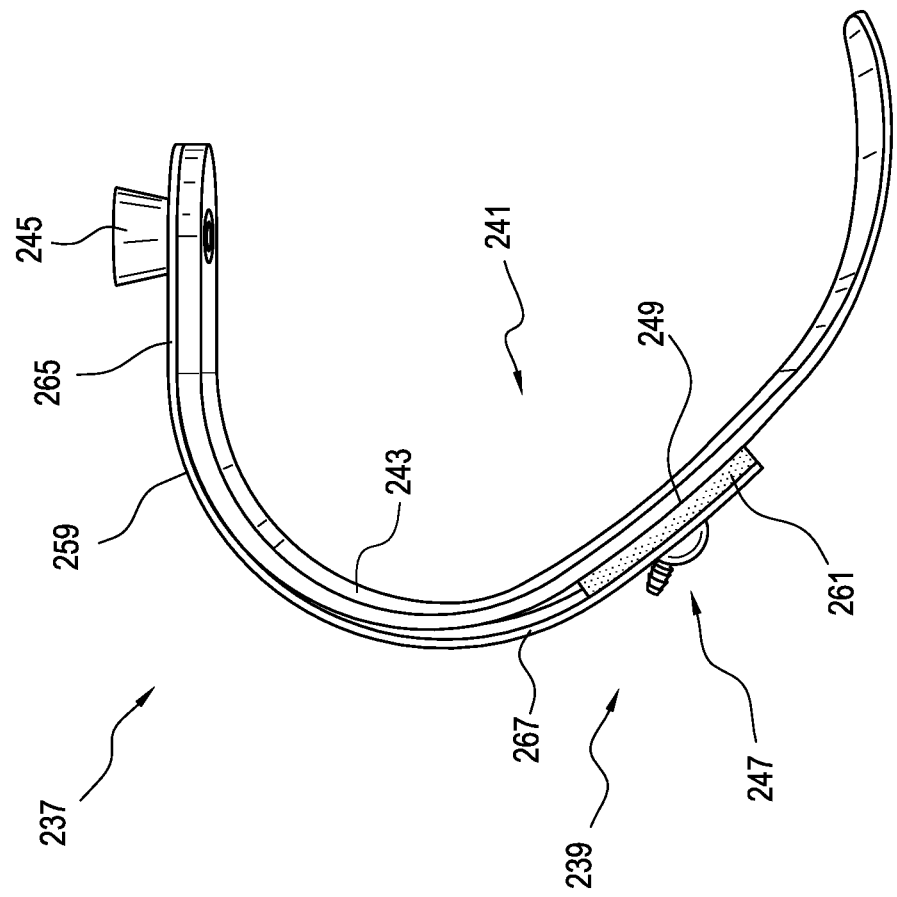
FIG. 14 shows a prosthetic system according to another embodiment.

FIGS. 14 and 15 illustrate yet another embodiment of a prosthetic system 237 including a pump system 239. As noted above, embodiments of the pump system can be adapted to fit prosthetic feet that are particularly difficult to operate with a conventional pump mechanism.

For instance, the prosthetic system 237 can include a prosthetic sport foot 241 arranged to efficiently store and release energy produced during running to improve performance. The prosthetic running foot 241 has a plate-like member 243 having an overall curved profile. A proximal portion of the plate-like member 243 can have an attachment adaptor 245 for connecting the prosthetic foot to a user's residual limb or to another prosthetic component (e.g., pylon, socket). The prosthetic running foot 241 can be a monolithic member made of a fiber material (e.g., carbon fiber). In other embodiments, the prosthetic running foot 241 can be modular and/or made of other suitable materials. The prosthetic running foot 241 shown is Össur Cheetah, however, it will be understood that the pump systems described herein can also be adapted for use with other prosthetic running feet and components.

The pump system 239 comprises a pump mechanism 247 having a suction cup type configuration. The pump mechanism 247 includes an elastomer membrane 249 arranged to be positioned on and form seal with a sealing surface 251 defined along a posterior aspect of the plate-like member 243. The membrane 249 has a compliant configuration.

The pump mechanism 247 relies upon deformation of the membrane 249 to move been an original configuration in which the volume of a fluid chamber 253 defined between the sealing surface 251 and a bottom of the membrane 249 is zero or near-zero, and an expanded configuration in which the volume of the fluid chamber 253 is increased. The membrane 249 can have any suitable configuration.

The membrane 249 defines a passageway 255 in fluid communication with the fluid chamber 253. In the illustrated embodiment, a fluid regulator or valve assembly 257 can be associated with the passageway 255. The valve assembly 257 is arranged to only allow fluid to enter the fluid chamber 253 via the passageway 255. The valve assembly 257 can comprise any suitable valve assembly. A housing 261 or fitting can be associated with the passageway 255. The housing 261 can be arranged to attach the pump mechanism 247 to a tube in fluid communication with a socket. The housing 261 can connect the membrane 249 to a support member described below.

As the pump mechanism 247 moves toward the original configuration, pressure within the fluid chamber 253 can increase until the seal between the membrane 249 and the sealing surface 251 is broken, allowing fluid in the fluid chamber 253 to escape or be expelled out under the sides of the membrane 249. The pump mechanism 247 thus does not require an outlet valve assembly, reducing the overall weight and profile of the pump system 239.

A support member 259 is arranged to move the pump mechanism 247 between the original and expanded configurations. The support member 259 can have a rigid configuration. The support member 259 can have any suitable shape but is shown having a curvature generally corresponding to the curvature of the plate-like member 243.

The support member 259 can be attached to a posterior side of the plate-like member 243. A proximal end portion 265 of the support member 259 is attached to the proximal end of the plate-like member 243. A distal end portion 267 of the support member 259 is attached to a center portion of the membrane 249. The support member 259 can define an opening or slot for connecting the membrane 249 to the support member 259.

During stance, the plate-like member 243 compresses and moves away from the distal end portion 267 of the support member 259, which, in turn, causes the support member 259 to pull the center portion of the membrane 249 away from the sealing surface 251, increasing the volume of the fluid chamber 253. This increase in volume of the fluid chamber 253 creates a vacuum in the pump mechanism 247, pulling fluid into the pump mechanism.

In swing or when the load is removed from the foot 247, stored energy in the plate-like member 243 expands the plate-like member 243 and moves it toward the distal end portion 267 of the support member 259, bringing the sealing surface 251 and the center portion of the membrane 249 together. During the return of the sealing surface 251 toward the center portion of the membrane 259, increased pressure in the fluid chamber 253 can break the seal between the membrane 259 and the sealing surface 251, allowing fluid in the fluid chamber 253 to be expelled out under the membrane 249.

The pump system can thus generate a vacuum in a socket using compression and expansion of a sport foot without undesirably affecting the functionality of the foot or significantly increasing the bulk of the running foot.

In addition, because the membrane 249 is compliant, the membrane 249 can create and maintain the seal between the bottom of the membrane 249 and the sealing surface 251 even as the sealing surface 251 moves and changes shape with the expansion and compression of the plate-like member 243. This advantageously allows the pump mechanism 247 to fit on a wider variety of surfaces, feet and prosthetic components.

According to a variation, the pump system 247 includes a closure-assist mechanism 271 arranged to bias the pump mechanism 247 toward the original configuration. In an embodiment, the closure-assist mechanism 271 can comprise a foam member 273 having a resilient configuration positioned between the interior surface of the support member 259 and the outer surface of the membrane 249.

As the pump mechanism 247 moves toward the expanded configuration, the foam member 273 is compressed between the membrane 249 and the support member 259, storing energy in the foam member 273. When the force on the membrane 249 is removed or reduced, the stored energy or resilient properties of the foam member 273 can force the center portion of the membrane 249 back toward the sealing surface 251, biasing the pump mechanism 247 toward the original configuration. Optionally, the center portion of the membrane 249 can be extend through an opening 277 defined in the foam member 263.

While various aspects and embodiments have been disclosed herein, other aspects and embodiments are contemplated. For instance, the membrane used in the embodiments described can vary in thickness in different areas and in shape. The membrane may be a cylindrical shape, a tapered shape, or any other suitable shape. In other embodiments, the pump mechanism can include a plurality of closure-assist mechanisms such as a magnetic closure element and a resilient closure element.

In yet other embodiments, the pump mechanism can be attached to a pylon, prosthetic ankle, or any other suitable prosthetic component. In other embodiments, embodiments of the pump system can include two, three, or any other suitable number of pump mechanisms. In embodiments where the pump system is associated with first and second parts rotatable about a joint, it will be appreciated that the first part may rotate relative to the second part, the second part may rotate relative to the first part, or both parts may rotate about the joint. Further, it will be appreciated that the pump system may be arranged to move the pump mechanism into the expanded configuration in stance, swing, or in both stance and swing.

In other embodiments, the pump mechanism can include one or more features arranged so that a user can regulate or control the level of vacuum generated by the pump mechanism. For instance, the pump mechanism can include a plurality of membranes having different stiffness and/or thickness that can be selected by a user to increase or decrease the volume change of the fluid chamber, which, in turn, controls the vacuum generated by the pump mechanism. In other embodiments, the pump mechanism may include an adjustable closure-assist mechanism that can be manipulated by a user to increase or decrease the level of force required to move the pump mechanism between the expanded and original configurations, which, in turn, controls the vacuum generated by the pump mechanism.

The various aspects and embodiments disclosed herein are for purposes of illustration and are not intended to be limiting. Additionally, the words "including," "having," and variants thereof (e.g., "includes" and "has") as used herein, including the claims, shall be open ended and have the same meaning as the word "comprising" and variants thereof (e.g., "comprise" and "comprises").

The invention claimed is:

1. A prosthetic system comprising:
   a support member having a flexible configuration defining a joint;
   first and second parts connected via the support member, the first and second parts rotatable relative to one another about the joint via deformation of the support member, and adapted to form at least part of a weight bearing connection between a prosthetic foot and a socket, wherein the first part comprises a proximal part of a prosthetic connector and the second part comprises a distal part of the prosthetic connector; and
   a pump system including a pump mechanism operatively connected to the first and second parts via the support member such that relative rotation between the first and second parts about the joint moves the pump mechanism between an original configuration in which a volume of a fluid chamber defined by the pump mechanism is zero or near-zero, and an expanded configuration in which the volume of the fluid chamber is increased.

2. The prosthetic system of claim 1, further comprising a movable member having a rigid configuration including a first end attached to the pump mechanism and a second end portion attached to the first part, wherein rotation of the movable member moves the pump mechanism between the original and expanded configurations.

3. The prosthetic system of claim 1, wherein the pump mechanism includes a housing and a membrane attached to the housing such that the fluid chamber is defined between the membrane and the housing.

4. The prosthetic system of claim 3, wherein deformation of the membrane increases the volume of the fluid chamber.

5. The prosthetic system of claim 1, wherein the support member is arranged to maintain a shape and support the proximal and distal parts a distance from one another when no load is placed on the prosthetic connector.

6. The prosthetic system of claim 1, wherein the support member is arranged to flex and pivot the first part relative to the second part when a load is placed on the prosthetic connector.

7. A prosthetic system comprising:
   a support member having a flexible configuration defining a joint;
   first and second parts connected via the support member, the first and second parts rotatable relative to one another about the joint via deformation of the support member, and adapted to form at least part of a weight bearing connection between a prosthetic foot and a socket, wherein the first part comprises a proximal part of a prosthetic connector and the second part comprises a distal part of the prosthetic connector; and
   a pump system including:
      a pump mechanism operatively connected to the first and second parts via the support member such that rotation between the first and second parts about the joint moves the pump mechanism between an original configuration in which a volume of a fluid chamber defined by the pump mechanism is zero or near-zero, and an expanded configuration in which the volume of the fluid chamber is increased; and
      a movable member having a rigid configuration including a first end portion connected to the pump mechanism and a second end portion connected to at least one of the first and second parts, wherein rotation between the first and second parts rotates the movable member relative to the pump mechanism.

* * * * *